United States Patent
Ikegami et al.

(10) Patent No.: US 9,962,651 B2
(45) Date of Patent: May 8, 2018

(54) DEVICE AND METHOD FOR GAS TREATMENT USING NON-THERMAL PLASMA AND CATALYST MEDIUM

(75) Inventors: Makoto Ikegami, Tokyo (JP); Takanori Matsumoto, Tokyo (JP); Tsuruo Nakayama, Tokyo (JP); Youhei Jikihara, Tokyo (JP)

(73) Assignee: NBC MESHTEC, INC., Tokyo (JP)

( * ) Notice: Subject to any disclaimer, the term of this patent is extended or adjusted under 35 U.S.C. 154(b) by 369 days.

(21) Appl. No.: 14/345,762

(22) PCT Filed: Sep. 4, 2012

(86) PCT No.: PCT/JP2012/005600
§ 371 (c)(1),
(2), (4) Date: Mar. 19, 2014

(87) PCT Pub. No.: WO2013/042328
PCT Pub. Date: Mar. 28, 2013

(65) Prior Publication Data
US 2014/0219894 A1    Aug. 7, 2014

(30) Foreign Application Priority Data
Sep. 21, 2011 (JP) ................ 2011-206650
Mar. 30, 2012 (JP) ................ 2012-082869

(51) Int. Cl.
*B01D 53/56* (2006.01)
*B01D 53/86* (2006.01)
(Continued)

(52) U.S. Cl.
CPC ............ *B01D 53/8687* (2013.01); *A61L 9/00* (2013.01); *B01D 53/32* (2013.01); *B01D 53/88* (2013.01);
(Continued)

(58) Field of Classification Search
None
See application file for complete search history.

(56) References Cited

U.S. PATENT DOCUMENTS 6,488,900 B1 *  12/2002  Call ....................... A62B 11/00
                                                422/120
2004/0118046 A1 *  6/2004  Williamson .......... B01J 19/088
                                                48/197 R
(Continued)

FOREIGN PATENT DOCUMENTS

JP    2000-139198    5/2000
JP    2000-140562    5/2000
(Continued)

OTHER PUBLICATIONS

JP 2007-144278A English Translation (Jun. 2007).*
(Continued)

*Primary Examiner* — Anita Nassiri Motlagh
(74) *Attorney, Agent, or Firm* — Wenderoth, Lind & Ponack, L.L.P.

(57) ABSTRACT

A gas treatment device includes a plasma-generating unit and a catalyst medium. The plasma-generating unit is provided with at least a flow channel through which a gas to be treated flows; and a power-supply unit for supplying electrical power, a first electrode, a second electrode and a dielectric material arranged inside the flow channel. A voltage is impressed between the first electrode and the second electrode by the power-supply unit and electrical discharging is caused to occur, whereby plasma is generated. The catalyst medium is adapted for accelerating a reaction with the gas to be treated and is provided in a position where the plasma generated by the plasma-generating unit inside the flow channel is present, and the catalyst medium has metallic catalytic particles present on an inorganic substance.

3 Claims, 12 Drawing Sheets

(51) Int. Cl.
| | |
|---|---|
| *A61L 9/00* | (2006.01) |
| *B01J 23/10* | (2006.01) |
| *B01J 23/42* | (2006.01) |
| *B01J 23/44* | (2006.01) |
| *B01J 23/52* | (2006.01) |
| *B01J 8/02* | (2006.01) |
| *B01D 53/32* | (2006.01) |
| *B01D 53/88* | (2006.01) |
| *B01J 23/34* | (2006.01) |
| *B01J 23/50* | (2006.01) |
| *B01J 23/72* | (2006.01) |

(52) U.S. Cl.
CPC ........... *B01J 8/02* (2013.01); *B01J 23/10* (2013.01); *B01J 23/34* (2013.01); *B01J 23/42* (2013.01); *B01J 23/44* (2013.01); *B01J 23/50* (2013.01); *B01J 23/52* (2013.01); *B01J 23/72* (2013.01); *B01D 2255/104* (2013.01); *B01D 2255/106* (2013.01); *B01D 2255/1021* (2013.01); *B01D 2255/1023* (2013.01); *B01D 2255/2065* (2013.01); *B01D 2255/20715* (2013.01); *B01D 2255/902* (2013.01); *B01D 2257/2064* (2013.01); *B01D 2257/70* (2013.01); *B01D 2257/708* (2013.01); *B01D 2257/7027* (2013.01); *B01D 2258/06* (2013.01); *B01D 2259/818* (2013.01)

(56) References Cited

U.S. PATENT DOCUMENTS

| | | |
|---|---|---|
| 2005/0118079 A1 | 6/2005 | Muroi et al. |
| 2005/0214181 A1 | 9/2005 | Kaneko et al. |
| 2009/0324443 A1 | 12/2009 | Whitehead et al. |

FOREIGN PATENT DOCUMENTS

| | | |
|---|---|---|
| JP | 2002-336343 | 11/2002 |
| JP | 2003-158996 | 6/2003 |
| JP | 2005-230627 | 9/2005 |
| JP | 2005-349247 | 12/2005 |
| JP | 2007-144278 | 6/2007 |
| JP | 2008-49280 | 3/2008 |
| JP | 2008-161838 | 7/2008 |
| JP | 2010-234195 | 10/2010 |
| JP | 2012-61393 | 3/2012 |
| RU | 2 184 601 | 7/2002 |

OTHER PUBLICATIONS

JP 2008-049280 A (English Translation), National Institute of Advanced Industrial Science and Technology (Mar. 6, 2008).*

Kim et al., "Complete Oxidation of Volatile Organic Compounds (VOCs) Using Plasma-Driven Catalysis and Oxygen Plasma", International Journal of Plasma Environmental Science & Technology, vol. 1, No. 1, Mar. 2007, pp. 46-51.*

English translation of International Preliminary Report on Patentability dated Apr. 3, 2014 in International (PCT) Application No. PCT/JP2012/005600.

International Search Report (ISR) dated Dec. 18, 2012 in International (PCT) Application No. PCT/JP2012/005600.

Atsushi Ogata et al., "Plasma Kudo Shokubai Hanno ni yoru VOC Bunkai", Chemical Engineering, vol. 55, No. 12, pp. 917-922, Dec. 1, 2010.

Extended European Search Report dated Apr. 6, 2016 in European Application No. 12832841.6.

* cited by examiner

DEVICE AND METHOD FOR GAS TREATMENT USING NON-THERMAL PLASMA AND CATALYST MEDIUM

TECHNICAL FIELD

The present invention relates to a device and a method for oxidation decomposition treatment of a hazardous gas using non-thermal plasma and a catalyst medium.

BACKGROUND ART

In recent years, as a method and a device for decomposition of a hazardous gas, methods and devices using non-thermal plasma have been proposed. Since the device using non-thermal plasma is simple and the non-thermal plasma is a chemical reaction in which an active species having a high reactivity can be used, the reaction instantaneously proceeds. For this reason, the non-thermal plasma is expected to effectively decompose a hazardous gas in a gas. Further, the non-thermal plasma is easily combined with other techniques. The non-thermal plasma is known to be applicable to various types of combined processes. However, when effective decomposition is not sufficient, a by-product is generated by the decomposition of a hazardous gas. For sufficiently effective decomposition, the input of a large amount of energy is required. In this case, there are problems of generation of nitrogen oxides and a large amount of ozone from air. In order to make a practical application of a technique for removing a hazardous gas in air by the non-thermal plasma, it is an important object to suppress the generation of nitrogen oxides and ozone and to improve the decomposition efficiency of the hazardous gas.

As achievement of such an object, a method for decomposing an ethylene gas using plasma (Patent Literatures 1 and 2), a method for providing a honeycomb-shaped catalyst between a discharge electrode and an earth electrode (ground electrode) (Patent Literature 3), and a method for providing a manganese-based catalyst (Patent Literature 4) have been proposed. Further, a method of further remedying the generation of ozone and the generation of by-products by decomposition of a hazardous gas in the conventional method of using non-thermal plasma in combination with a known catalyst and a device for purifying the hazardous gas (Patent Literature 5) have been proposed.

Citation List

Patent Literature

Patent Literature 1: Japanese Patent Application Laid-Open No. 2000-139198
Patent Literature 2: Japanese Patent Application Laid-Open No. 2003-158996
Patent Literature 3: Japanese Patent Application Laid-Open No. 2000-140562
Patent Literature 4: Japanese Patent Application Laid-Open No. 2002-336343
Patent Literature 5: Japanese Patent Application Laid-Open No. 2005-230627

The regeneration of an adsorbent in a short time is required for a gas purification method based on adsorption. In a conventional method for regenerating an adsorbent, facilities for desorption by steam and desorption by heating are necessary. Therefore, the facilities may be enlarged, and a drainage facility may be required according to a desorption method. In a method for providing pellets of a ferroelectric material between a discharge electrode and an earth electrode, a high voltage needs to be applied depending on the particle diameter of a dielectric material and filling amount of the dielectric material. This results in problems of generation of hazardous ozone and nitrogen oxides from air. Further, in a method for providing a honeycomb-shaped catalyst, the catalyst needs to surely come into contact with a hazardous gas. Therefore, a distance between a discharge electrode and an earth electrode is elongated. In addition, in order to stably generate plasma, a high voltage needs to be applied to produce a large amount of energy. As a result, there are problems of generation of nitrogen oxides and a large amount of ozone from air. In a method proposed by the present inventors, an adsorbent having a metallic catalytic function is used. In this case, there is a problem in which the concentration of a hazardous gas to be treated is limited depending on the amount of the adsorbent having a metallic catalytic function. When a pellet-shaped or honeycomb-shaped catalyst is disposed, it is difficult that a purification device is flexibly designed in terms of the structure.

SUMMARY OF THE INVENTION

The present invention has been made to solve the problems. It is an object of the present invention to provide a device and a method for oxidation decomposition treatment of a hazardous gas of a volatile organic compound (VOC) or the like at normal temperature.

Solution to Problem

A first aspect of the present invention is a gas treatment device provided with: a flow channel through which a gas to be treated flows;
a plasma-generating unit provided with at least a first electrode, a second electrode, a dielectric material, and a power-supply unit for supplying electric power, which are arranged inside the flow channel, wherein a voltage is applied between the first electrode and the second electrode by the power-supply unit to cause electrical discharging to occur, whereby plasma is generated; and
a catalyst medium which is provided in a position where the plasma generated by the plasma-generating unit inside the flow channel is present, is adapted for accelerating a reaction with the gas to be treated, and has metallic catalytic particles present on an inorganic substance.

A second aspect of the present invention is the gas treatment device according to the first aspect of the present invention, wherein the first electrode, the second electrode, the dielectric material, and the catalyst medium are arranged in order in a flow direction of the gas to be treated, and are each permeable in the flow direction of the gas, and the catalyst medium is disposed in a space where the electrical discharging is caused to occur in the flow channel or on a downstream side of the space in the flow direction of the gas.

A third aspect of the present invention is the gas treatment device according to the first aspect of the present invention, wherein the first electrode, the second electrode, the dielectric material, and the catalyst medium are arranged in order in a direction perpendicular to the flow direction of the gas.

A fourth aspect of the present invention is the gas treatment device according to any one of the first to third aspects of the present invention, wherein the catalyst medium is further provided with a substrate to which at least the metallic catalytic particles are fixed and which is made of an inorganic material.

A fifth aspect of the present invention is the gas treatment device according to any one of the first to third aspects of the present invention, wherein the catalyst medium is further provided with:

inorganic particles to the surface of which the metallic catalytic particles are fixed; and a substrate to which the inorganic particles are fixed and which is made of an inorganic material.

A sixth aspect of the present invention is the gas treatment device according to any one of the first to third aspects of the present invention, wherein the catalyst medium is filled with a large number of inorganic particles supporting the metallic catalytic particles.

A seventh aspect of the present invention is the gas treatment device according to any one of the first to sixth aspects of the present invention, wherein the first electrode and the second electrode are each a comb-teeth-shaped electrode that is formed from a large number of electrodes extending in respective predetermined directions, and the gas to be treated flows through a space formed by the comb-teeth-shaped electrodes, the dielectric material, and the catalyst medium.

An eighth aspect of the present invention is the gas treatment device according to any one of the first to seventh aspects of the present invention, wherein the plasma is at least one kind of discharge plasma of silent discharge, creeping discharge, corona discharge, and pulse discharge.

A ninth aspect of the present invention is the gas treatment device according to any one of the first to eighth aspects of the present invention, wherein the metallic catalytic particles are made of at least one kind of Pt, Au, $CeO_2$, PdO, $MnO_2$, CuO, and Ag.

A tenth aspect of the present invention is the gas treatment device according to any one of the first to ninth aspects of the present invention, wherein the power-supply unit supplies electrical power at an output frequency of 0.5 kHz or higher.

An eleventh aspect of the present invention is a gas treatment method including: generating plasma by electrical discharging in a range where a catalyst medium for accelerating an oxidation decomposition reaction with a gas to be treated is disposed; and passing the gas to be treated in the plasma to cause oxidation decomposition.

A twelfth aspect of the present invention is the gas treatment method according to the eleventh aspect of the present invention, wherein electrical power is supplied at an output frequency of 0.5 kHz or higher to cause electrical discharging to occur, whereby the plasma is generated.

Advantageous Effects of Invention

In the gas treatment device in the present invention, a catalyst and plasma are used in combination. This allows a gas containing a hazardous substance or the like to be converted into $CO_2$ by oxidation decomposition at low temperature without leaving reaction intermediates such as CO and formaldehyde. Further, the plasma prevents the adsorption of impurities, reaction intermediates, and the like to the catalyst surface. Therefore, the degradation of catalytic performance can be suppressed and a catalytic activity can be maintained for extended periods. In addition, a substrate for fixing a catalyst is made of an inorganic material. Thus, the substrate is resistant to plasma, and a catalyst medium can be used for extended periods. Accordingly, the present invention can provide a gas treatment device capable of effectively oxidizing and decomposing a hazardous substance of a volatile organic compound (VOC) or the like that pollutes an environment and adversely affects the human body.

DESCRIPTION OF EMBODIMENTS

Hereinafter, embodiments of the present invention will be described.

First Embodiment

Figure 1:
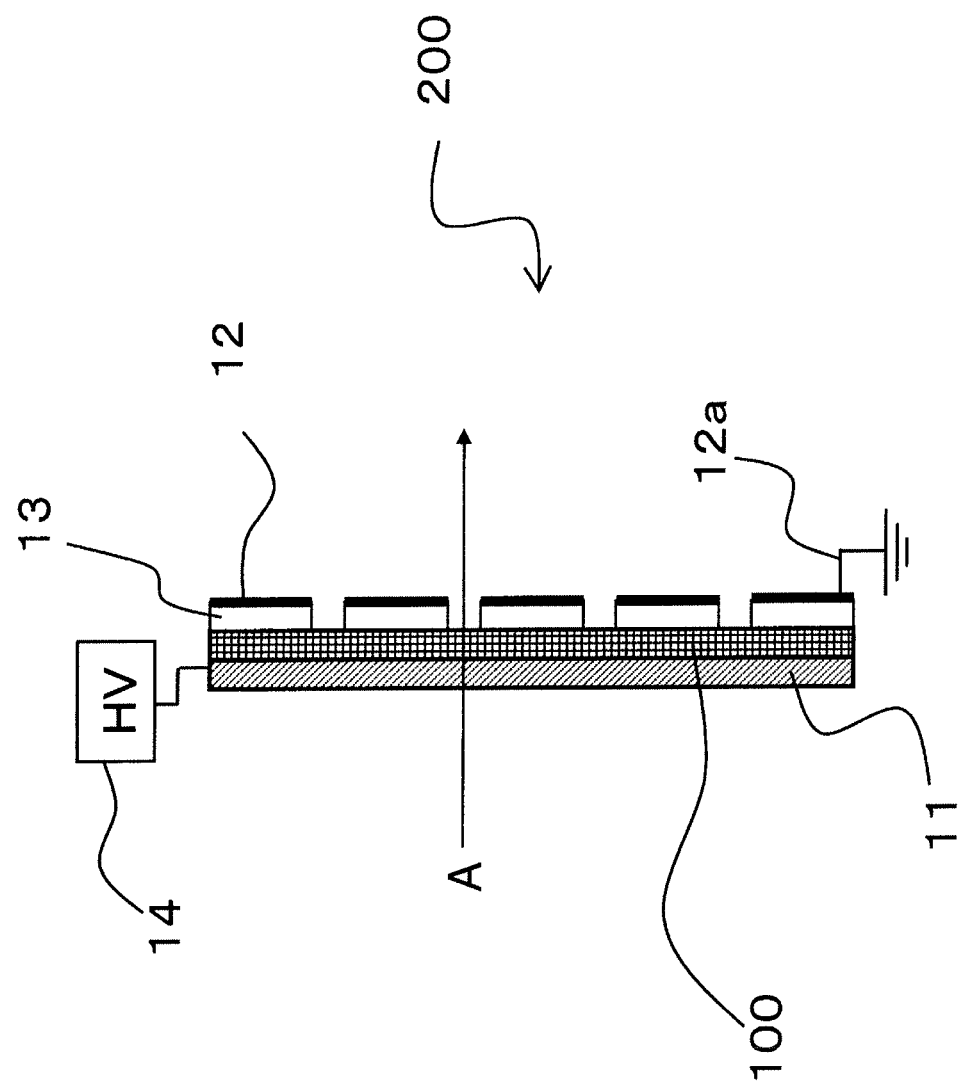
FIG. 1 is a schematic cross-sectional view of a gas treatment device according to an embodiment of the present invention.

FIG. 1 is a view schematically illustrating the cross section of a gas treatment device 200 according to an embodiment of the present invention. The gas treatment device 200 is disposed inside a flow channel supplied with a gas containing a gas to be treated. In FIG. 1, the gas treatment device 200 is a device in which a gas containing a gas to be treated that is supplied to the gas treatment device 200 in an arrow A direction is converted into $CO_2$ by oxidation decomposition using plasma generated in the gas treatment device 200 and the function of a catalyst medium 100.

The gas treatment device 200 is provided with an application electrode 11, a ground electrode 12, a dielectric material 13, a catalyst medium 100, and a (high-voltage) power supply 14 as a power-supply unit. In the gas treatment device 200, the application electrode 11, the ground electrode 12, the dielectric material 13, and the power supply 14 constitute a member and a device (plasma-generating unit) for generating plasma. When a voltage is applied by the power supply 14, a non-thermal plasma reaction layer is formed by electrical discharging occurring between the application electrode 11 and the dielectric material 13 by the application electrode 11, the ground electrode 12, and the dielectric material 13. In the gas treatment device 200, the application electrode 11, the catalyst medium 100, the ground electrode 12, and the dielectric material 13 are configured to be in close contact with one another. One of the application electrode 11 and the ground electrode 12 is a first electrode and the other is a second electrode. In other embodiments, a plurality of application electrodes 11 and a plurality of ground electrodes 12 are combined. Even in these cases, one kind of electrodes are each a first electrode and the other kind of electrodes are each a second electrode.

The application electrode 11 is an electrode to which a voltage is applied by the power supply 14. The ground electrode 12 is grounded by a ground wire 12a. The application electrode 11, the ground electrode 12, and the dielectric material 13 have a permeable structure in which a gas can pass through the electrodes. Specific examples of the structures of the application electrode 11, the ground electrode 12, and the dielectric material 13 may include a lattice structure, a reed screen structure, a porous structure processed by punching, and an expanded mesh structure. As the structures, a combination of two or more of these structures may be used. The application electrode 11 and the ground electrode 12 may have an acicular structure. The application electrode 11, the ground electrode 12, and the dielectric material 13 may have the same shape and structure among the above-described shapes and structures. In FIG. 1, the application electrode 11 has many small apertures like a mesh, and the ground electrode 12 and the dielectric material 13 have a small number of large apertures like a porous structure processed by punching.

As the application electrode 11 and the ground electrode 12, a material functioning as an electrode can be used. As materials for the application electrode 11 and the ground electrode 12, for example, a metal such as Cu, Ag, Au, Ni, Cr, Fe, Al, Ti, W, Ta, Mo, and Co and an alloy thereof can be used.

The dielectric material 13 may have a property to be an insulator. Examples of the material for the dielectric material 13 may include an inorganic material such as $ZrO_2$, $\gamma$-$Al_2O_3$, $\alpha$-$Al_2O_3$, $\theta$-$Al_2O_3$, $\eta$-$Al_2O_3$, amorphous $Al_2O_3$, alumina nitride, mullite, steatite, forsterite, cordierite, magnesium titanate, barium titanate, SiC, $Si_3N_4$, Si—SiC, mica, and glass, and a polymeric material such as polyimide, liquid crystal polymer, poly tetra fluoro ethylene (PTFE), ethylene tetra fluoro ethylene (ETFE), polyvinyl fluoride (PVF), poly vinylidene difluoride (PVDF), polyetherimide, and polyamide imide. In terms of plasma resistance and heat resistance, an inorganic material is more preferable.

When the catalyst medium 100 described below has a function as a dielectric material (for example, when a portion of the catalyst medium is an insulator), the catalyst medium 100 can be used as a dielectric material. In this case, the dielectric material 13 may not be provided.

Figure 2:
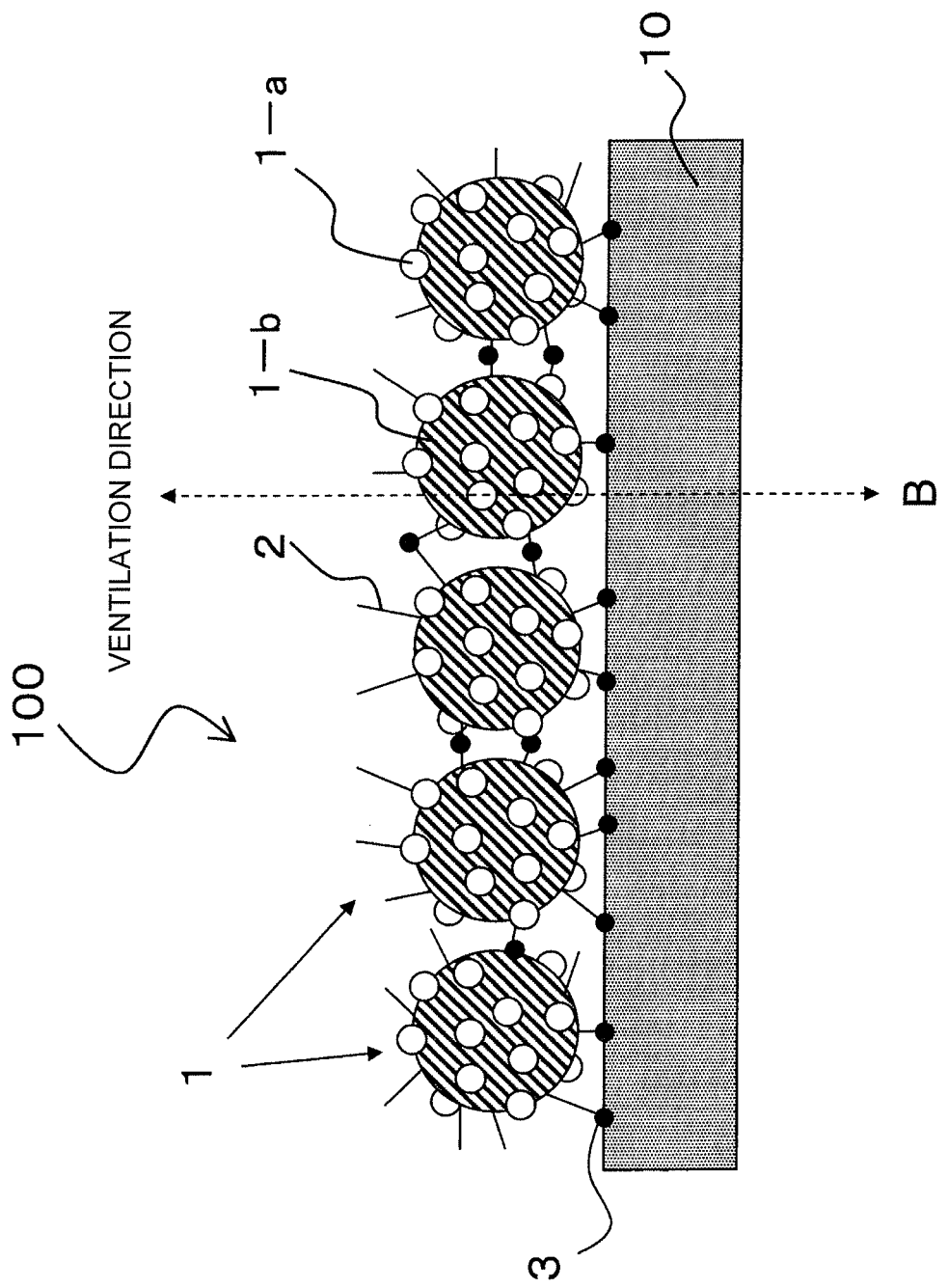
FIG. 2 is a schematic view of a catalyst medium to which catalyst fine particles are fixed, according to the embodiment of the present invention.

Next, the catalyst medium 100 will be described. FIG. 2 is a view schematically illustrating a portion of the cross section of the catalyst medium 100 according to the embodiment. The catalyst medium 100 is a catalyst for accelerating a reaction in which a gas to be treated is converted into carbon dioxide ($CO_2$) by oxidation decomposition. In the embodiment, since the catalyst medium 100 is subjected to plasma, an oxidation decomposition reaction accelerated by the catalyst medium 100 is further accelerated.

The catalyst medium 100 of the present embodiment is a permeable plate-shaped or sheet-shaped member through which gas can pass. The catalyst medium 100 is configured to include a substrate 10, a catalyst 1 fixed to the substrate 10, and the like. The catalyst medium 100 is disposed in a position (region) where plasma generated by the plasma-generating unit is present. In the present embodiment, the catalyst medium 100 is specifically disposed between the application electrode 11 and the dielectric material 13 (in a discharge space). A gas can pass through the catalyst medium 100 in directions of a double-headed dashed-line arrow B in FIG. 2. For this reason, the catalyst medium 100 of the present embodiment has a structure in which the catalyst 1 is fixed to the substrate 10 so as to maintain permeability. The substrate 10 has permeable structure such as a filter structure, a mesh structure, or a structure in which a plurality of holes are formed on a plate shaped member by perforation such as punching. It is preferable that the catalyst medium 100 be disposed so that a face fixing the catalyst 1 is oriented toward a side of the application electrode 11 (an upstream side of gas flow direction) in the gas treatment device 200. For example, when the substrate 10 has a filter-shaped or mesh-shaped structure, a space can be formed inside the substrate 10. In this case, the catalyst 1 can be fixed to the inside of the substrate 10 according to a method for producing the catalyst medium 100. Alternatively, the catalyst 1 may be fixed to both faces of the substrate 10. When the catalyst 1 is fixed to the inside of the substrate 10 or to the both faces of the substrate 10, the catalyst medium 100 may be disposed toward either direction.

In the catalyst 1, catalyst fine particles 1-$a$ are supported by carrier fine particles 1-$b$. The catalyst 1 is fixed to the substrate 10 by binding silane monomers 2 bound to each of the carrier fine particles 1-$b$ to the substrate 10 through chemical bonds 3. The fixation using the silane monomers 2 will be described below.

The catalyst fine particles 1-$a$ of the catalyst 1 are not limited as long as they have a catalytic function for accelerating a reaction in which a gas to be treated is converted into $CO_2$ by oxidation decomposition. It is preferable that the catalyst fine particles be made of Au, Pt, $CeO_2$, PdO, $MnO_2$, or CuO, that has a high oxidation catalytic function.

The catalyst fine particles 1-$a$ may have a particle diameter of about 0.5 nm or larger and about 200 nm or smaller. The amount of the catalyst fine particles 1-$a$ to be fixed to the carrier fine particles 1-$b$ is preferably 0.1 to 20% by mass, and more preferably 0.5 to 10% by mass. When 20% by mass or more of the catalyst fine particles are supported, catalyst fine particles that are the catalyst fine particles 1-$a$ are aggregated. This is because the catalytic activity is low. When the amount is 0.1% by mass or less, the catalytic activity is not sufficiently obtained. Therefore, this range is not preferable.

The catalyst fine particles 1-$a$ need to include a fine particle having a catalytic function for accelerating a reaction in which at least a gas to be treated is converted into carbon dioxide by oxidation decomposition as described above, but the catalyst fine particles 1-$a$ may be combined with another substance. Specifically, the catalyst fine particles 1-$a$ may be a mixture of catalyst fine particles and promoter fine particles, or a composite catalyst including composite fine particles obtained by combining various metal elements with catalyst fine particles. When the catalyst fine particles are singly used or when a promoter is mixed in the catalyst fine particles, the catalyst fine particles may have a polyhedral shape and the sizes thereof may fall within the above-described range. When composite fine particles combined with another metal element are used, the size of the catalyst fine particles may fall within the above-described range. Examples of metal fine particles (nanoparticles) other than the catalyst fine particle used for the promoter or the composite catalyst may include noble metal such as Pt, Pd, and Ir and an oxide thereof, and base metal and an oxide thereof. Two or more kinds of fine particles of noble metal and an oxide thereof and base metal and an oxide thereof may be mixed and supported by the surface of the carrier fine particles 1-*b*.

The carrier fine particles 1-*b* are particles which support the catalyst fine particles 1-*a* and through which the catalyst fine particles 1-*a* are fixed to the substrate 10. The carrier fine particles 1-*b* are not limited to particular ones as long as the particles can support the catalyst fine particles 1-*a*. It is preferable that as the carrier fine particles 1-*b*, a metal oxide or an inorganic compound mainly having a physical absorptive property be used.

Examples of the metal oxide may include a single inorganic oxide such as $\gamma$-$Al_2O_3$, $\alpha$-$Al_2O_3$, $\theta$-$Al_2O_3$, $\eta$-$Al_2O_3$, amorphous $Al_2O_3$, $TiO_2$, $ZrO_2$, $SnO_2$, $SiO_2$, $MgO$, $ZnO_2$, $Bi_2O_3$, $In_2O_3$, $MnO_2$, $Mn_2O_3$, $Nb_2O_5$, $FeO$, $Fe_2O_3$, $Fe_3O_4$, $Sb_2O_3$, $CuO$, $Cu_2O$, $NiO$, $Ni_3O_4$, $Ni_2O_3$, $CoO$, $Co_3O_4$, $Co_2O_3$, $WO_3$, $CeO_2$, $Pr_6O_{11}$, $Y_2O_3$, $In_2O_3$, $PbO$, and $ThO_2$. For example, the metal oxide may be a composite oxide such as $SiO_2$—$Al_2O_3$, $SiO_2$—$B_2O_3$, $SiO_2$—$P_2O_5SiO_2$—$TiO_2$, $SiO_2$—$ZrO_2$, $Al_2O_3$—$TiO_2$, $Al_2O_3$—$ZrO_2$, $Al_2O_3$—$CaO$, $Al_2O_3$—$B_2O_3$, $Al_2O_3$—$P_2O_5$, $Al_2O_3$—$CeO_2$, $Al_2O_3$—$Fe_2O_3$, $TiO_2$—$CeO_2$, $TiO_2$—$ZrO_2$, $TiO_2$—$WO_3$, $ZrO_2$—$WO_3$, $SnO_2$—$WO_3$, $CeO_2$—$ZrO_2$, $SiO_2$—$TiO_2$—$ZrO_2$, $Al_2O_3$—$TiO_2$—$ZrO_2$, $SiO_2$—$Al_2O_3$—$TiO_2$, or $SiO_2$—$TiO_2$—$CeO_2$, or a cerium-zirconium-bismuth composite oxide. A cerium-zirconium-bismuth composite oxide is a solid solution represented by a general formula: $Ce_{1-X-Y}Zr_XBi_YO_{2-\delta}$, wherein X, Y, and $\delta$ fall within a range of $0.1 \leq X \leq 0.3$, $0.1 \leq Y \leq 0.3$, and $0.05 \leq \delta \leq 0.15$, respectively.

Examples of the inorganic compound having a physical absorptive property may include a silicate including synthesis zeolite such as zeolite A, zeolite P, zeolite X, and zeolite Y, natural zeolite such as clinoptilolite, cepiolite, and mordenite, a layered silicate compound such as kaolinite, montmorillonite, acid clay, and kieselguhr, and a cyclic silicate compound such as wollastonite and neptunite. Examples thereof may further include a phosphate compound including tricalcium phosphate, calcium hydrogen phosphate, calcium pyrophosphate, calcium metaphosphate, and hydroxyapatite, activated carbon, and porous glass.

The carrier fine particles 1-*b* to be used are selected depending on the kind of gas to be treated. The average particle diameter of the carrier fine particles 1-*b* may be 0.1 μm or larger and 500 μm or smaller. The carrier fine particles 1-*b* may be used singly or two or more kinds thereof may be used in a mixture. The average particle diameter used herein refers to a volume average particle diameter. Unless otherwise noted, the average particle diameter herein represents a volume average particle diameter.

A method for producing the catalyst 1 will be described. This method for producing the catalyst 1 may be a method in which the catalyst fine particles 1-*a* have a polyhedral structure and the catalyst fine particles 1-*a* can be fixed to the carrier fine particles 1-*b*. Examples of the method may include a coprecipitation method, a deposition-precipitation method, a sol-gel method, a neutralization-precipitation method using dropping, a reductant addition method, a neutralization-precipitation method using pH-control, and a carboxylic acid metal salt addition method. The methods can be appropriately used depending on the kind of carrier.

The substrate 10 is a substrate constituting the catalyst medium 100 as a plate-shaped member to which the catalyst 1 is fixed. The substrate 10 has a permeable structure as described above. For example, a sheet-shaped substrate having many through pores formed by punching, or a fibrous, cloth-shaped, or mesh-shaped substrate having a fibrous structure (filter-shaped) that is made of woven fabric, knitting, or nonwoven fabric can be used. In addition, substrates having various shapes and sizes can be appropriately used depending on intended use.

It is preferable that the substrate 10 be made from an inorganic material having excellent plasma resistance and heat resistance. The plasma resistance is required since the substrate 10 is disposed in a region where plasma is present. When the substrate 10 has plasma resistance, the catalytic function of the catalyst medium 100 can be maintained for extended periods. The heat resistance is required since the gas to be treated in the gas treatment device 200 may be an exhaust gas that is discharged during burning a fuel and has a comparatively high temperature. When the exhaust gas is treated, the substrate needs to have heat resistance. The plasma resistance is a durability in an atmosphere of plasma, and shows difficulty of occurrence of erosion by plasma.

It is preferable that the inorganic material used for the substrate 10 be specifically a metal material, ceramics, or glass, and more preferably metal, a metal oxide, or glass. In the present embodiment, the carrier fine particles 1-*b* supporting the catalyst fine particles 1-*a* are fixed to the substrate 10 through the silane monomers 2. When the silane monomers 2 are fixed to the substrate 10 by a dehydration-condensation reaction through a covalent bond, it is preferable that a thin film of an oxide be formed on the surface of the substrate 10.

As the metal material used for the substrate 10 of the present invention, metal having a high melting point such as tungsten, molybdenum, tantalum, niobium, titanium zirconiummolybdenum (TZM), and tungsten-rhenium (W—Re), noble metal such as silver and ruthenium and an alloy or an oxide thereof, special metal such as titanium, nickel, zirconium, chromium, inconel, and hastelloy, general-purpose metal such as aluminum, copper, stainless steel, zinc, magnesium, and iron, an alloy including the general-purpose metal, or an oxide of the general-purpose metal may be used. Further, a member having a film of the metal, the alloy, or the oxide formed by various plating, vacuum evaporation, a CVD method, or a sputtering method may be used as the metal material.

A naturally oxidized thin film is generally formed on the surface of the metal and the surface of the alloy. In order to bind the silane monomers 2 thereto, the naturally oxidized thin film can be used. In this case, it is preferable that oils and dirt adhering to the surface of the oxidized thin film be removed by an ordinary method in advance. This is because the carrier fine particles 1-*b* can be fixed stably and uniformly. Instead of use of the naturally oxidized film for binding of the silane monomers 2, an oxidized thin film may be formed on the surface of the metal or the surface of the alloy by a known chemical method or a known electro-chemical method such as anodic oxidation.

As ceramics used for the substrate 10 of the present invention, ceramic ware such as earthenware, pottery, stoneware, and porcelain, and ceramics such as glass, cement, gypsum, enamel, or fine ceramics can be used. As the composition of the ceramics, element-based, oxide-based, hydroxide-based, carbide-based, carbonate-based, nitride-based, halide-based, or phosphate-based ceramics may be used, or a composite thereof may be used.

As ceramics used for the substrate 10 of the present invention, barium titanate, lead zirconate titanate, ferrite, alumina, forsterite, zirconia, zircon, mullite, steatite, cordierite, aluminum nitride, silicon nitride, silicon carbide, new carbon, new glass, or ceramics such as high strength ceramics, functional ceramics, superconducting ceramics, nonlinear optical ceramics, antimicrobial ceramics, biodegradable ceramics, and bioceramics can be used.

As glass used for the substrate 10 of the present invention, glass such as soda-lime glass, potash glass, crystal glass, quartz glass, chalcogen glass, uranium glass, water glass, polarization glass, tempered glass, laminated glass, heat-resistant glass/borosilicate glass, bulletproof glass, glass fiber, dichronic glass, goldstone (red goldstone, aventurine, blue goldstone), glass ceramics, glass having a low melting point, metal glass, or saphiret can be used.

In addition, as the substrate 10 of the present invention, cement can be used. The cement includes ordinary portland cement, high-early-strength portland cement, ultra high-early-strength portland cement, medium-heat portland cement, low-heat portland cement, sulfate resisting portland cement, portland blast furnace cement that are mixed cement obtained by adding blast furnace slag, fly ash, and siliceous admixture to portland cement, silica cement, fly ash cement and the like.

Further, as the substrate 10 of the present invention, titania, zirconia, alumina, ceria (cerium oxide), zeolite, apatite, silica, activated carbon, kieselguhr, or the like can be used. As the inorganic oxide in the present embodiment, an oxide of metal such as chromium, manganese, iron, cobalt, nickel, copper, and tin can be used.

Next, a method for fixing the catalyst 1 to the substrate 10 will be described. The catalyst 1 in the present embodiment is held on the substrate 10 by binding the silane monomers 2 that are bound to the surface of the carrier fine particles 1-$b$ supporting the catalyst fine particles 1-$a$ to the substrate 10 through chemical bonds 3 (covalent bond) formed by a dehydration-condensation reaction.

A mechanism in which the carrier fine particles 1-$b$ supporting the catalyst fine particles 1-$a$ are bound to the substrate 10 through the silane monomers 2 will be described. The silane monomers 2 bound to the carrier fine particles 1-$b$ are oriented with an unsaturated bond site or a reactive functional group facing outward from the carrier fine particles 1-$b$, and then bound. This is because a hydrophilic silanol group at one end of each of the silane monomers 2 is attracted to the hydrophilic surface of the carrier fine particles 1-$b$. On the other hand, since the unsaturated bond site or the reactive functional group at the other end is hydrophobic, it tends to be located away from the surface of the carrier fine particles 1-$b$. Thus, the silanol group of each of the silane monomers 2 is covalently bound to the surface of the carrier fine particles 1-$b$ by a dehydration-condensation reaction, and as a result, the silane monomers 2 are likely to be oriented with the unsaturated bond site or the reactive functional group facing outward. Therefore, many silane monomers 2 are covalently bound to carrier fine particles 1-$b$ with the unsaturated bond sites or the reactive functional groups facing outward. The unsaturated bond sites or the reactive functional groups of the silane monomers 2 that are bound to the surface of the carrier fine particles 1-$b$ while facing outward are bound to one another. As a result, the carrier fine particles 1-$b$ are bound to one another. In addition, the unsaturated bond sites or the reactive functional groups are also bound to the surface of the substrate 10, to thereby fix the carrier fine particles 1-$b$ to the substrate 10.

In other words, the silane monomers 2 that each have an unsaturated bond site or a reactive functional group and are excellent in reactivity are used in the catalyst medium 100 used in the embodiment. Therefore, a plurality of carrier fine particles 1-$b$ above the substrate 10 are bound to one another through the chemical bonds 3 between the unsaturated bond sites or the reactive functional groups of the silane monomers. Further, the chemical bonds 3 are formed by the unsaturated bond site or the reactive functional group between the silane monomers 2 on the surface of the carrier fine particles 1-$b$ facing the substrate 10 and the surface of the substrate 10. As a result, the carrier fine particles 1-$b$ are fixed to the substrate 10.

Examples of the unsaturated bond site or the reactive functional group of each of the silane monomers 2 that are covalently bound to the carrier fine particles 1-$b$ by dehydration condensation may include a vinyl group, an epoxy group, a styryl group, a methacrylo group, an acryloxy group, and an isocyanate group.

Examples of the above silane monomers 2 having the unsaturated bond site or the reactive functional group may include vinyltrimethoxysilane, vinyltriethoxysilane, vinyltriacetoxysilane, N-β-(N-vinylbenzylaminoethyl)-γ-aminopropyltrimethoxysilane, hydrochloride of N-(vinylbenzyl)-2-aminoethyl-3-aminopropyltrimethoxysilane, 2-(3,4-epoxycyclohexyl)ethyltrimethoxysilane, 3-glycidoxypropyltrimethoxysilane, 3-glycidoxypropylmethyldiethoxysilane, 3-glycidoxypropyltriethoxysilane, p-styryltrimethoxysilane, 3-methacryloxypropylmethyldimethoxysilane, 3-methacryloxypropyltrimethoxysilane, 3-methacryloxypropylmethyldiethoxysilane, 3-methacryloxypropyltriethoxysilane, 3-acryloxypropyltrimethoxysilane, and 3-isocyanatepropyltriethoxysilane.

Next, a method for producing the catalyst medium 100 by fixing the catalyst 1 to the substrate 10 will be described.

The silane monomers 2 having an unsaturated bond site or a reactive functional group are caused to be covalently bound to the carrier fine particles 1-$b$ supporting the catalyst fine particles 1-$a$. The silane monomers 2 can be bound to the carrier fine particles 1-$b$ by a general method. For example, a method may include adding the silane monomer 2 to a dispersion solution in which the carrier fine particles 1-$b$ supporting the catalyst fine particles 1-$a$ are dispersed in a dispersion medium such as water, methanol, ethanol, methyl ethyl ketone (MEK), acetone, xylene, or toluene, and heating under reflux to thereby covalently bind the silane monomers 2 to the surface of the carrier fine particles 1-$b$ by a dehydration-condensation reaction.

Another method will be as follows. The carrier fine particles 1-$b$ supporting the catalyst fine particles 1-$a$ are pulverized into finer particles. The finer particles are dispersed in any one of the above described dispersion media to obtain a dispersion solution. The silane monomers 2 are added to the dispersion solution. Alternatively, the silane monomers 2 are added to the carrier fine particles 1-$b$ supporting the catalyst fine particles 1-$a$, the mixture is pulverized into finer particles, and the finer particles are dispersed in a dispersion media. The dispersion solution is subjected to solid-liquid separation, and the resultant product is heated at 100° C. to 180° C., so that the silane monomers 2 are covalently bound to the surfaces of the carrier fine particles 1-$b$ by a dehydration condensation reaction.

The amount of the silane monomers 2 in the catalyst 1 depends on the average particle diameter of the carrier fine particles 1-$b$. However, when the amount is 0.01% by mass or more and 40.0% by mass or less relative to the amount of the carrier fine particles 1-$b$, the bond strength of bonds between the carrier fine particles 1-$b$ and between the carrier fine particles 1-$b$ and the substrate 10 are sufficient for practical application. Further, excess silane monomers 2 not relating to the binding may be present.

Subsequently, the carrier fine particles 1-*b* to the surface of which the silane monomers 2 are chemically bound are mixed and dispersed in a dispersion medium such as methanol, ethanol, methyl ethyl ketone (MEK), acetone, xylene, and toluene. In order to accelerate the dispersion, a surfactant, mineral acid such as hydrochloric acid and sulfuric acid, carboxylic acid such as acetic acid and citric acid, or the like, may be added, if necessary. Next, the carrier fine particles 1-*b* are crushed and dispersed with an apparatus such as a beads mill, a ball mill, a sand mill, a roll mill, a vibration mill, or a homogenizer in the dispersion medium, to produce a slurry containing the carrier fine particles 1-*b*.

The slurry which is obtained as described above and in which the carrier fine particles 1-*b* are dispersed is applied to the surface of the substrate 10. A method for applying the slurry to the substrate 10 is not particularly limited as long as the slurry can be applied according to the purpose, and the slurry may be applied by a spin coating method, a dip coating method, a spray coating method, a cast coating method, a bar coating method, a microgravure coating method, or a gravure coating method, which is generally used.

If necessary, the dispersion medium is removed by heating and drying. As a result, the carrier fine particles 1-*b* are chemically bound to the substrate 10. Specifically, the dispersion medium is removed to form chemical bonds 3 between the silane monomers 2 on the surface of the carrier fine particles 1-*b*. Thus, the carrier fine particles 1-*b* are bound to one another, and the chemical bonds 3 are formed between the silane monomers 2 and the substrate 10. As a result, the carrier fine particles 1-*b* are fixed to the substrate 10.

In the present embodiment, it is preferable that as a method for binding the silane monomers 2 to the substrate 10 through the chemical bond 3, a binding method by graft polymerization be used. Examples of an applicable graft polymerization may include graft polymerization using a peroxide catalyst, graft polymerization using thermal or light energy, and graft polymerization using radiation (radiation graft polymerization). The graft polymerization to be used is appropriately selected according to the shapes and the configurations of the substrate 10 and the carrier fine particles 1-*b*.

For efficient and uniform graft polymerization of the silane monomers 2, the surface of the substrate 10 may previously be subjected to hydrophilic treatment including corona discharge treatment, plasma discharge treatment, flame treatment, and chemical treatment with an aqueous solution of an oxidizing acid such as chromic acid or perchloric acid, or an aqueous alkaline solution containing sodium hydroxide.

The catalyst medium and the production method are described above. According to the catalyst medium 100 described above, the carrier fine particles 1-*b* bound to the substrate 10 are strongly held on the substrate 10 through the silane monomers 2. Therefore, separation of the catalyst 1 from the substrate 10 can be surely prevented.

The power supply 14 used in the gas treatment device 200 is a power supply which can apply a high voltage. As the power supply 14, a power supply of high voltage such as AC high voltage and pulse high voltage, a power supply superimposing AC voltage or pulse voltage on a DC bias, or the like can be used. Examples of AC high voltage may include sine wave alternating-current voltage, rectangular wave alternating-current voltage, triangular wave alternating-current voltage, and sawtooth wave alternating-current voltage. A predetermined voltage may be applied to the application electrode 11 and the ground electrode 12 by the power supply 14 so that plasma is generated in a discharge space formed by the application electrode 11, the ground electrode 12, and the dielectric material 13. The voltage applied by the power supply 14 varies depending on the concentration of the gas to be treated, or the like, and is generally 1 to 20 kV, and preferably 2 to 10 kV. The kind of electrical discharging occurring by electrical power supplied by the power supply 14 to generate plasma is not particularly limited as long as plasma can be generated. For example, the electrical discharging may be silent discharge, creeping discharge, corona discharge, pulse discharge, or the like. Two or more kinds of the discharges may be combined to generate plasma.

It is preferable that the output frequency of the power supply be high frequency, and the output frequency may be specifically 0.5 kHz or higher. The output frequency is preferably 0.5 kHz or higher and 15 kHz or lower, and more preferably 1 kHz or higher and 10 kHz or lower. When the frequency is lower than 0.5 kHz, the amount of intermediate products and ozone to be produced is increased. When the frequency is higher than 15 kHz, the oxidation decomposition of any gas to be treated is suppressed.

The configuration of the gas treatment device 200 of the present embodiment is described above.

Next, the oxidation decomposition treatment of a gas by the gas treatment device 200 in the present embodiment will be described. The gas to be treated in the gas treatment device 200 of the present embodiment is a gas containing at least any of a volatile substance contained in a fuel and a solvent such as a volatile organic compound (VOC), and carbon monoxide. The gas to be treated is a mixed gas containing a plurality of kinds of gases, or a single gas. Specific examples, of VOC may include aromatic hydrocarbons such as benzene, xylene, toluene, ethylbenzene, styrene, p-dichlorobenzene, and di-2-ethylhexyl phthalate, a compound having a C=O double bond (carbonyl group) including ketones such as acetone and methyl ethyl ketone (MEK), alcohols such as isopropyl alcohol and methanol, esters such as ethyl acetate and di-n-butyl phthalate, and aldehydes such as formaldehyde and acetaldehyde. Examples thereof may further include alkanes such as ethylene and tetradecane, organic phosphorus compounds such as chlorpyrifos and diazinon, trichloroethylene, and tetrachloroethylene.

The preferable output frequency of the power supply for use in generation of plasma varies depending on the gas to be treated. When a component of the gas to be treated is previously specified, the output frequency may be set according to the gas. Specifically, when the gas is CO, the output frequency is preferably 0.5 kHz or higher and 15 kHz or lower. When the gas is alkane such as ethylene, the output frequency is preferably 0.5 kHz or higher and 7 kHz or lower, and when the gas is another VOC, the output frequency is preferably 0.5 kHz or higher and 15 kHz or lower. When the output frequency falls within the range, intermediate products and ozone are not produced, and the gas to be treated is oxidized and decomposed. Therefore, when the output frequency is set within the range in case of a gas having been specified, the gas can be surely subjected to the oxidation decomposition treatment without intermediate products and ozone being generated.

In order to treat the gas, a voltage is applied to the application electrode 11 by the power supply 14. In this state, a gas containing the gas to be treated is supplied in a direction from the application electrode 11 side to the ground electrode 12 side (arrow A direction) in FIG. 1. Thus, the gas to be treated is oxidized at normal temperature using plasma and a catalyst without heating to thereby be decomposed into $CO_2$. When only a catalyst is used, the surface of the catalyst fine particles is poisoned by contact with the gas. As a result, the catalytic activity may be lost, carbon monoxide that has not been converted into $CO_2$ may be left, and reaction intermediates such as formaldehyde may be generated. However, when the catalyst is used in combination with plasma, the catalytic surface is cleaned and the catalytic activity is maintained. Furthermore, reaction intermediates are hardly produced, and the gas to be treated is converted into $CO_2$ by oxidation decomposition.

The gas treatment device 200 of the present embodiment can treat the gas to be treated and decompose it into $CO_2$ to make it harmless, and discharge the harmless gas to air at normal temperature. Examples of VOC that is a gas capable of being treated by the gas treatment device 200 of the present embodiment may include substances volatilized from organic solvents in a coating material, an adhesive, a cleaner, and the like, that are used in a factory or an office. Examples thereof may further include substances volatilized from a fuel such as heavy oil, kerosene, liquefied petroleum gas (LPG), and manufactured gas, and an unburned gas during burning of the fuel. Additional examples may include ethylene generated from an agricultural product. In addition, examples thereof may further include substances volatilized from interior materials of vehicle, residential building materials and interior materials, and materials such as a housing and a member of consumer electronics. For example, carbon monoxide that is the gas to be treated is generated by incomplete combustion at a combustion process in a factory or a kitchen, or in a home heating appliance. A gas containing such a gas to be treated flows through the catalyst medium 100 and is simultaneously subjected to plasma. Thus, the gas to be treated can effectively be converted into $CO_2$ by oxidation decomposition without heating to be made harmless, and the harmless gas can be discharged to air.

The present embodiment has been described such that the gas treatment device 200 is provided with the catalyst 1 as the independent catalyst medium 100. However, the present invention is not limited to the present embodiment. The plasma-generating unit may be configured to be integrated with the catalyst medium. Specifically, the catalyst 1 may be configured so that the catalyst fine particles 1-a are fixed to the surface of the application electrode 11, the ground electrode 12, or the dielectric material 13. The configurations may be combined.

The present embodiment has been configured so that the dielectric material 13 comes into close contact with the ground electrode 12, but the present invention is not limited to the present embodiment. The present invention is not limited as long as plasma can be generated, and the dielectric material 13 may come into close contact with at least one of the application electrode 11 and the ground electrode 12. Further, a dielectric material 13 may be disposed in close contact with the application electrode 11 and another dielectric material 13 may be disposed in close contact with the ground electrode 12, and the catalyst medium 100 may be disposed between the two dielectric materials 13.

The present embodiment has been described such that the catalyst medium 100 is disposed between the application electrode 11 and the dielectric material 13, but the present invention is not limited to the embodiment. When the catalyst medium 100 is present in a position where plasma is present in a gas flow channel, a reaction in which the gas to be treated is converted into $CO_2$ by oxidation decomposition can be accelerated. For this reason, the catalyst medium 100 may be disposed on the downstream side of the plasma-generating unit including the application electrode 11, the dielectric material 13, and the ground electrode 12 in the gas flow direction.

The present embodiment has been described such that the application electrode 11 is disposed at the upstream side in the gas flow direction, but the present invention is not limited to the embodiment. A gas may flow from the ground electrode 12 side.

The present embodiment has been described such that the carrier fine particles 1-b supporting the catalyst fine particles 1-a are fixed by a silane compound such as the silane monomer 2, but the present invention is not limited to the embodiment. The carrier fine particles 1-b may be fixed by a binder including a common resin. The known fixing method such as Van der Waals force and physical adsorption may be used in addition to a chemical bond.

In the gas treatment device 200 of the present embodiment described above, the gas to be treated can be effectively oxidized and decomposed by combination of plasma with the catalyst medium 100 for accelerating a reaction in which the gas to be treated is oxidized and decomposed. Further, even when the catalyst 1 is poisoned in a process of decomposition treatment, the catalyst 1 is cleaned by plasma. Therefore, the catalytic activity of the catalyst medium 100 can be maintained for extended periods. In the gas treatment device 200 according to the present embodiment, the gas to be treated can be stably subjected to oxidation decomposition for extended periods. Further, in the present embodiment, if the carrier fine particles 1-b bound to the substrate 10 are bound to the substrate 10 through the silane monomers 2, the catalyst 1 is strongly fixed to the substrate 10. Therefore, separation can be suppressed. Accordingly, the catalyst 1 can be prevented from falling, and the oxidation decomposition performance of the gas 15, to be treated can be maintained for extended periods.

Second Embodiment

Figure 3:
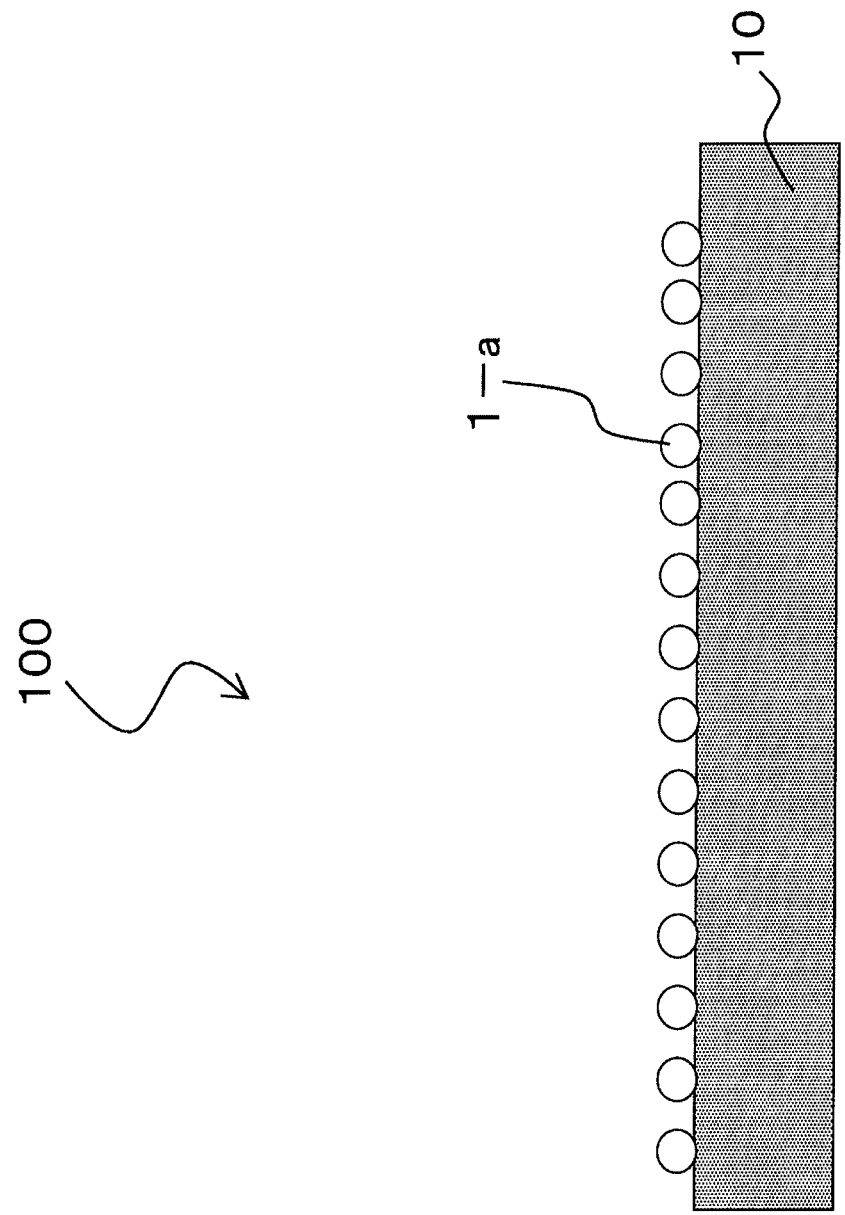
FIG. 3 is a schematic view of a catalyst medium according to another embodiment of the present invention.

A second embodiment will next be described. FIG. 3 is a view schematically illustrating a portion of the cross section of a catalyst medium 100 according to the present embodiment. Hereinafter, the description of the same components as those in the first embodiment will be omitted by denoting the same symbol.

In the catalyst medium 100 of the present embodiment, catalyst fine particles 1-a are fixed to the surface of a substrate 10 by Van der Waals force, physical adsorption, or the like. The catalyst fine particles 1-a of the present embodiment are not fixed to inorganic fine particles but directly fixed to the surface of the substrate 10. It is preferable that the particle diameter of the catalyst fine particles 1-a be the same as that in the first embodiment.

The amount of the catalyst fine particles 1-a to be supported by the substrate 10 is preferably 0.5 to 20% by mass, and more preferably 0.5 to 10% by mass, relative to the amount of the substrate 10. This is because when the amount is 20% by mass or more, the catalyst fine particles 1-a are aggregated to decrease the catalytic activity.

A method for supporting the catalyst fine particles 1-a on the substrate 10 is not particularly limited. Specific examples of the method may include a coprecipitation method, a deposition-precipitation method, a sol-gel method, a neutralization-precipitation method using dropping, a reductant addition method, a neutralization-precipitation method using pH-control, and a carboxylic acid metal salt addition method. The methods can be appropriately used depending on the kind of carrier.

Hereinafter, a method for adjusting a catalyst medium of the present invention will be specifically described with reference to a deposition-precipitation method. In the deposition-precipitation method, while an aqueous solution containing a gold compound dissolved therein is first heated at a temperature of 20 to 90° C., and preferably 50 to 70° C. with stirring, the pH of the solution is adjusted to 3 to 10, and preferably 5 to 8 with an alkaline solution. The adjusted solution was added to a substrate 10, and then heated and dried at 100 to 200° C.

Examples of the gold compound aqueous solution may include $HAuCl_4 \cdot 4H_2O$, $NH_4AuCl_4$, $KAuCl_4 \cdot nH_2O$, $KAu(CN)_4$, $Na_2AuCl_4$, $KAuBr_4 \cdot 2H_2O$, and $NaAuBr_4$. The concentration of the gold compound is preferably $1 \times 10^{-2}$ to $1 \times 10^{-5}$ mol/L.

According to the present embodiment, the catalyst fine particles 1-*a* are directly fixed to the substrate 10. Therefore, the substrate itself serves as a carrier. Further, carrier fine particles are not necessary, and an effect of suppressing the aggregation of catalyst fine particles can be obtained.

In the present embodiment, the catalyst fine particles 1-*a* may be mixed particles with a promoter, or composite particles.

In the catalyst medium 100, in addition to the catalyst fine particles 1-*a*, fine particles of an oxide of manganese, cobalt, or the like may be further supported on the surface of the substrate 10. This is because the oxide fine particles suppress the adhesion of a hazardous substance to the catalyst fine particles 1-*a* to stably maintain the catalytic activity over extended periods. In particular, the oxide fine particles can prevent a hazardous substance of inorganic substance that is not decomposed by plasma from adhering to the catalyst fine particles 1-*a*, and therefore are effective. In the present embodiment, gold (Au) is used as the catalyst fine particles 1-*a*. However, even when Pt, $CeO_2$, PdO, or the like, exemplified in the first embodiment is used, the catalyst medium 100 can be produced similarly.

Third Embodiment

Figure 4:
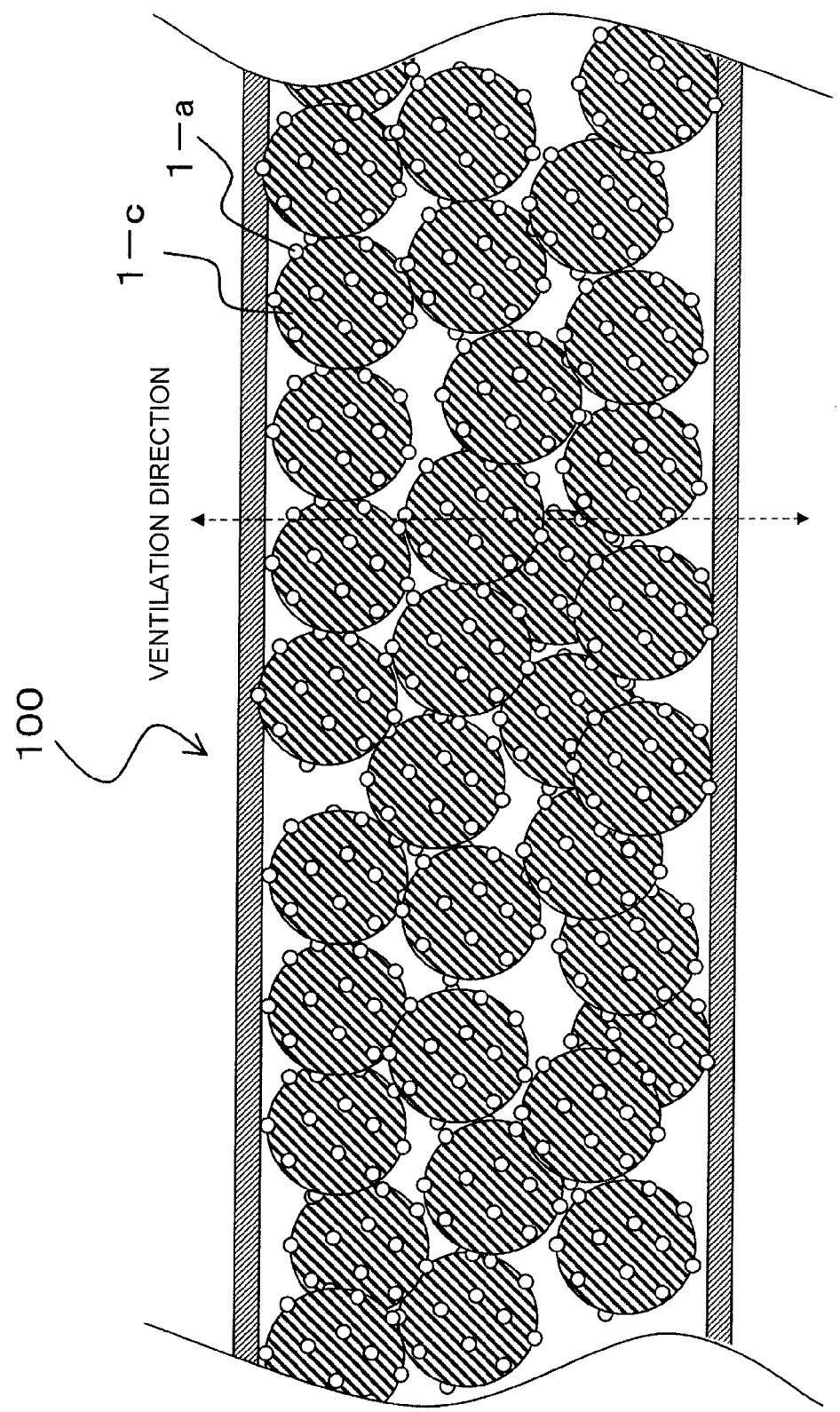
FIG. 4 is a schematic view of a catalyst medium according to another embodiment of the present invention.

Next, a third embodiment will be described. FIG. 4 is a view schematically illustrating a portion of the cross section of a catalyst medium 100 according to the embodiment. In the catalyst medium 100 of the third embodiment, a container which is permeable in a ventilation direction is filled with a large amount of inorganic particles 1-*c* to which catalyst fine particles 1-*a* are fixed. When a gas containing a gas to be treated flows in the ventilation direction shown in FIG. 4, the gas passes through a space between the inorganic particles 1-*c*, and comes into contact with the catalyst fine particles 1-*a* on the inorganic particles 1-*c*. As a result, an oxidation decomposition reaction is accelerated to convert the gas to be treated into $CO_2$. The container for the inorganic particles 1-*c* supporting the catalyst fine particles 1-*a* of the present embodiment may have a structure in which the permeability is maintained and the inorganic particles 1-*c* do not leak outside. For example, in the structure, a face through which the gas passes inward and a face through which the gas passes outward may have an aperture with a size smaller than the particle diameter of the inorganic particles 1-*c*. A material for the container is not particularly limited, and the material for the substrate 10 in the above-described embodiment may be used.

As a material for the inorganic particles 1-*c* of the present embodiment, the same substance as that in the inorganic particles 1-*b* may be used. The material to be used is selected depending on the kind of gas to be decomposed. The average particle diameter of the inorganic particles 1-*c* may be 100 µm or larger and 5,000 µm or smaller, and preferably 100 µm to 1,000 µm. The inorganic particles may be used singly or two or more kinds thereof may be used in a mixture.

The catalyst fine particles 1-*a* are fixed to the surface of the inorganic particles 1-*c*. The method for producing composite particles of the inorganic particles 1-*c* and the catalyst fine particles 1-*a* (when they are used in combination with other functional fine particles, composite particles of the inorganic particles 1-*c* as base particles, the catalyst fine particles 1-*a*, and the other functional fine particles are produced) is not particularly limited as long as the inorganic particles 1-*c* can be combined with the catalyst fine particles 1-*a*. For example, when the inorganic particles 1-*c* and sub-particles (catalyst fine particles 1-*a*) are mixed in a mortar, composite particles in which the catalyst fine particles 1-*a* are embedded in the inorganic particles 1-*c* can be formed. Further, the composite particles can be formed by a mechanochemical method. Examples of the mechanochemical method may include a high-speed airflow impact method in which the inorganic particles 1-*c* collide with the catalyst fine particles 1-*a* to mechanically bind the inorganic particles 1-*c* to the sub-particles, and a surface fusion method in which a high pressure is applied to the inorganic particles 1-*c* and the catalyst fine particles 1-*a* to bind the inorganic particles 1-*c* to the catalyst fine particles 1-*a* by the generated energy.

As a device capable of forming composite particles by embedding the catalyst fine particles 1-*a* in the inorganic particles 1-*c* for fixation, a general-purpose ball mill is exemplified. Additional examples of the device may include a rotary blade-type device including a super mixer manufactured by KAWATA MFG CO., Ltd., and a shaking-type device including PAINT SHAKER manufactured by ASADA IRON WORKS. CO., LTD. In addition, Hybridization System (registered trademark) manufactured by Nara Machinery Co., Ltd., Mechanofusion (registered trademark) manufactured by Hosokawa Micron Corporation, and a media slurry dryer may be exemplified. However, the device is not particularly limited to the above-described device.

In another mixing method, for example, a tumbling ball mill, a high-speed rotary pulverizer, a high-speed airflow impact-type pulverizer, a media agitating mill, or a mechanical fusion device may be used. As an operation factor of the high-speed rotary pulverizer, an agitation speed, a media amount, an agitation time, and the like are adjustment. By the adjustment, a degree (depth) of embedding the catalyst fine particles 1-*a* in the inorganic particles 1-*c* can be adjusted. As an operation factor of the high-speed airflow impact-type pulverizer, a pressure of carrier gas, a residence time, and the like are adjusted. By the adjustment, a degree of embedding the catalyst fine particles 1-*a* in the inorganic particles 1-*c* can be adjusted.

In a combination process, the inorganic particles 1-*c* and the catalyst fine particles 1-*a* are supplied to a combined device capable of producing composite fine particles as described above so that the ratio of the catalyst fine particles 1-*a* relative to the inorganic particles 1-*c* is 0.5% by mass or more and less than 40% by mass. In a combination process using the device, composite fine particles of antiviral agent having a smooth surface can be formed by adjustment of an agitation time or the like. In the combination process, the catalyst fine particles 1-*a* are embedded in the inorganic particles 1-*c*. The formed composite fine particles collide with each other to embed the catalyst fine particles 1-*a* in the inorganic particles 1-c more deeply. As a result, a smooth surfaces is formed so that the catalyst fine particles 1-a do not protrude from the surface of the inorganic particles 1-c.

According to the present embodiment, the catalyst fine particles 1-a are supported by the inorganic particles 1-c having a comparatively large particle diameter. For this reason, the catalyst fine particles 1-a are not aggregated. Further, since the particle diameter is large, the particles are unlikely to be scattered. Therefore, it is not necessary that the catalyst fine particles be fixed to a substrate.

Fourth Embodiment

Figure 5:
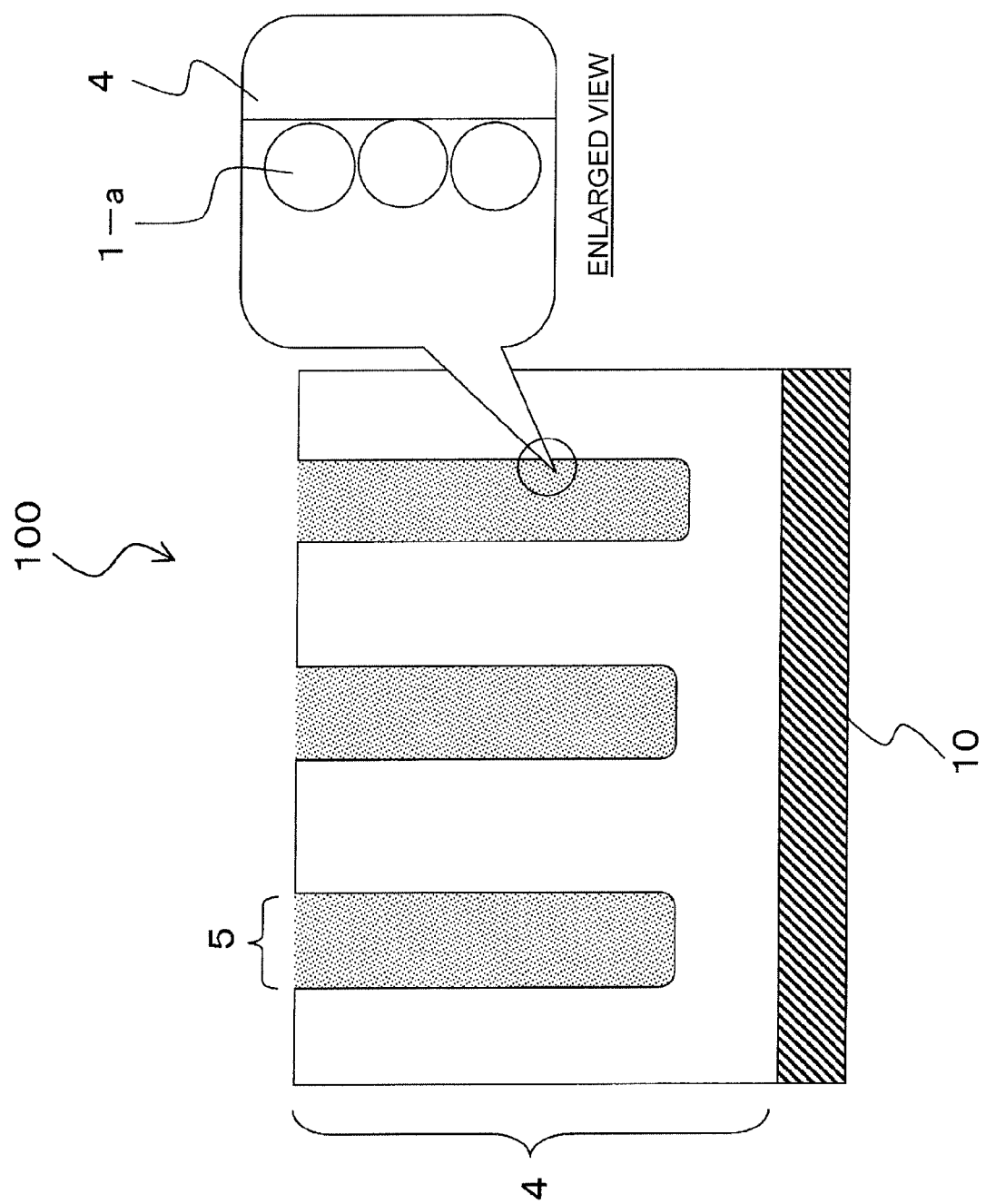
FIG. 5 is a schematic view of a catalyst medium according to another embodiment of the present invention.

A fourth embodiment will next be described. FIG. 5 is a view schematically illustrating a portion of the cross section of a catalyst medium 100 according to the present embodiment. In the catalyst medium 100 of the present embodiment, catalyst fine particles 1-a are fixed to the inside of micropores of a porous oxide film.

In the catalyst medium 100 of the present embodiment, an oxide film 4 is formed on the surface of a substrate 10. In the oxide film 4, many micropores 5 are formed. Each of the micropores 5 formed in the oxide film 4 is filled with the catalyst fine particles 1-a. Since the catalyst medium 100 needs to be permeable, a plurality of holes through the catalyst medium 100 are formed by punching. It is preferable that the catalyst medium 100 of the present embodiment be disposed so that the catalyst medium 100 on the oxide film 4 side is opposed to an electrode and is oriented toward an upstream side of a gas flow direction in the gas treatment device 200.

In the catalyst medium 100, a metal plate is subjected to anodic oxidation treatment to form an oxide film, and fixed to the surface of the substrate 10 formed from any materials exemplified in the first embodiment by adhesion. Alternatively, a metal plate as the substrate 10 is oxidized to form an oxide film 4 on the surface of the substrate 10. Examples of the metal plate may include aluminum, tantalum, niobium, titanium, hafnium, zirconium, zinc, tungsten, bismuth, and antimony. Since a micropore is easily formed by anodic oxidation, aluminum and titanium are preferred. Although the shape of the metal plate is not particularly limited, the whole thickness thereof is preferably 0.05 to 1.0 mm, more preferably 0.08 to 0.35 mm, and further preferably 0.1 to 0.3 mm.

As an oxidation method, any known method can be used. For example, a method in which electric current is passed through a metal plate on which an oxide film is formed as an anode in a solution with an acid concentration of 1 to 10% by mass can be used. As the solution used in the anodic oxidation treatment, for example, an aqueous solution of phosphoric acid, chromic acid, oxalic acid, sulfuric acid, citric acid, malonic acid, or tartaric acid can be used. In order to control crystallinity, heat treatment may be performed. When an oxide film having a crystallinity such as γ-alumina or α-alumina is formed, a method in which spark discharge is performed on aluminum in an aqueous solution containing sodium carbonate or sodium phosphate, or a method of performing anodic oxidation in a molten salt containing sodium hydrogen sulfate and ammonium hydrogen sulfate can be used. Depending on a metal material of the metal plate, micropores 5 are formed by anodic oxidation. Depending on conditions such as an applied voltage, a process temperature, a process time, and the like in the oxidation, the diameter of the micropores 5, the distance between the micropores, the film thickness, and the like can be adjusted.

The catalyst fine particles 1-a are adsorbed on the surface of the oxide film 4. Further, the catalyst fine particles 1-a are fixed to the oxide film 4 so that the particles are not desorbed even by contact with a gas to be treated. A method for fixing the catalyst fine particles 1-a to the oxide film 4 is not particularly limited, and known methods such as a deposition-precipitation method, a deposition-reduction method, an impregnation method, an ion exchange method, a coprecipitation method, a deposition method, a kneading method, a hydrothermal synthesis method, and a gas-phase synthesis method can be employed.

According to the present embodiment, when the catalyst fine particles 1-a are fixed to the metal material, the particles are fixed to the surface of the oxide film 4. Therefore, an effect of strong fixation can be obtained. In particular, when the catalyst fine particles 1-a are fixed to the inside of the micropores 5 formed by anodic oxidation treatment, the particles are more strongly fixed to the catalyst medium 100. Therefore, the catalyst fine particles 1-a can be prevented from falling and the catalytic effect can be stably obtained for extended periods.

The present embodiment has been described such that the catalyst fine particles 1-a are directly supported to the oxide film 4, but the present invention is not limited to the embodiment. Carrier fine particles 1-b may be precipitated on the surface of the oxide film 4, and the catalyst fine particles 1-a may be supported by the surface of the carrier fine particles 1-b. However, production using the method in which the catalyst fine particles 1-a are directly supported to the oxide film 4 is easy.

Fifth Embodiment

Figure 6:
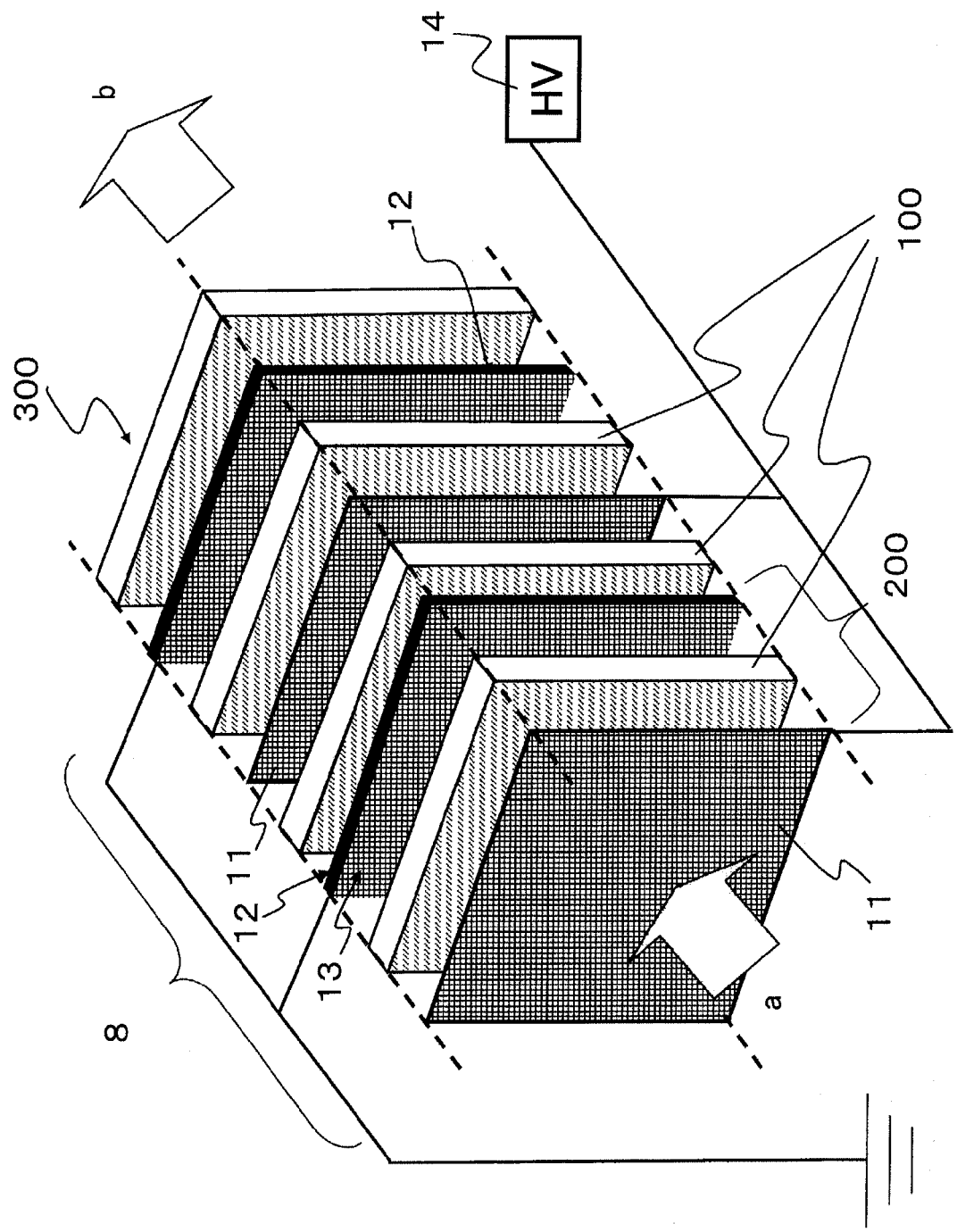
FIG. 6 is a schematic view of a gas treatment device according to another embodiment of the present invention.

A fifth embodiment will next be described. FIG. 6 is a schematic view of a gas treatment device 300 of the present embodiment. The present embodiment is another embodiment of the gas treatment device. Specifically, the gas treatment device 300 of the present embodiment has a configuration in which a plurality of gas treatment devices 200 described in the first embodiment are layered in a flow direction of a gas to be treated.

In the present embodiment, the gas treatment device 300 has a plurality of application electrodes 11, a plurality of ground electrodes 12, a plurality of dielectric materials 13, a plurality of catalyst media 100, and a power supply 14. In the gas treatment device 300 of the present embodiment, a non-thermal plasma reaction layer 8 is configured by arranging the application electrodes 11, the ground electrodes 12, and the dielectric materials 13 alternately. Each of the catalyst media 100 supporting catalyst fine particles is disposed between the application electrode 11 and the ground electrode 12 in the non-thermal plasma reaction layer 8. A set of the application electrode 11, the catalyst medium 100, the dielectric material 13, and the ground electrode 12 corresponds to the gas treatment device 200 of the first embodiment. The plurality of application electrodes 11 or the plurality of ground electrodes 12 serves as a first electrode and the other serves as a second electrode. Further the plurality of application electrodes 11, the plurality of ground electrodes 12, the plurality of dielectric materials 13, and the power supply 14 constitute a plasma-generating unit.

A gas to be treated flows into the gas treatment device 300 in an arrow a direction, and a decomposed gas is discharged from the device in an arrow b direction. In the gas treatment device 300, the plasma reaction layer 8 has a multilayer structure in which the application electrodes 11, the ground electrodes 12, and the catalyst media 100 are layered. Each of the catalyst media 100 supporting a catalyst is provided in each of the layers, to form a multilayer structure. Therefore, the gas to be treated or the like can be highly oxidized and decomposed between the electrodes.

According to the present embodiment, a large amount of the gas can be effectively oxidized and decomposed due to the multilayer structure.

Sixth Embodiment

Figure 7:
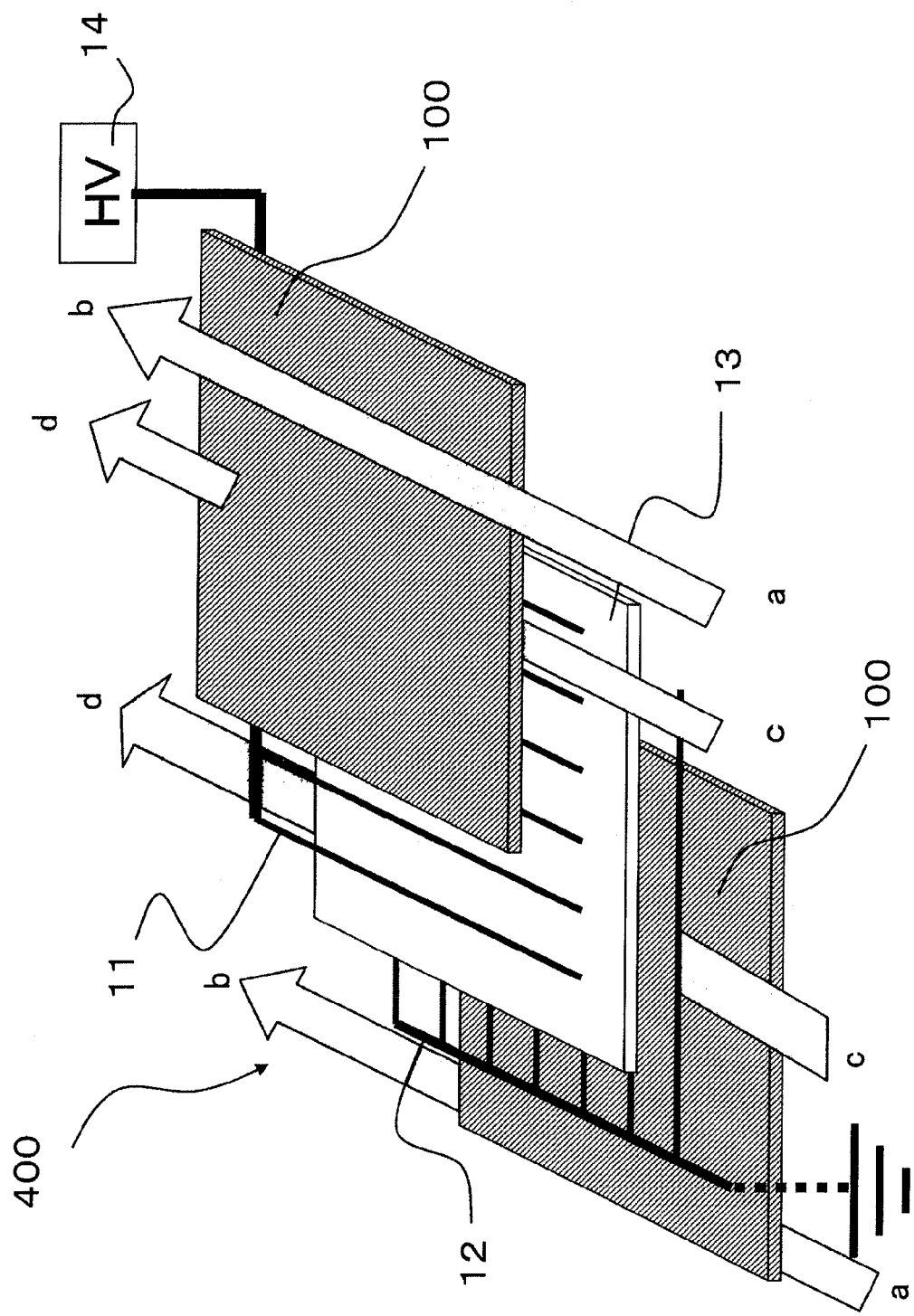
FIG. 7 is a schematic view of a gas treatment device according to another embodiment of the present invention.
Figure 8:
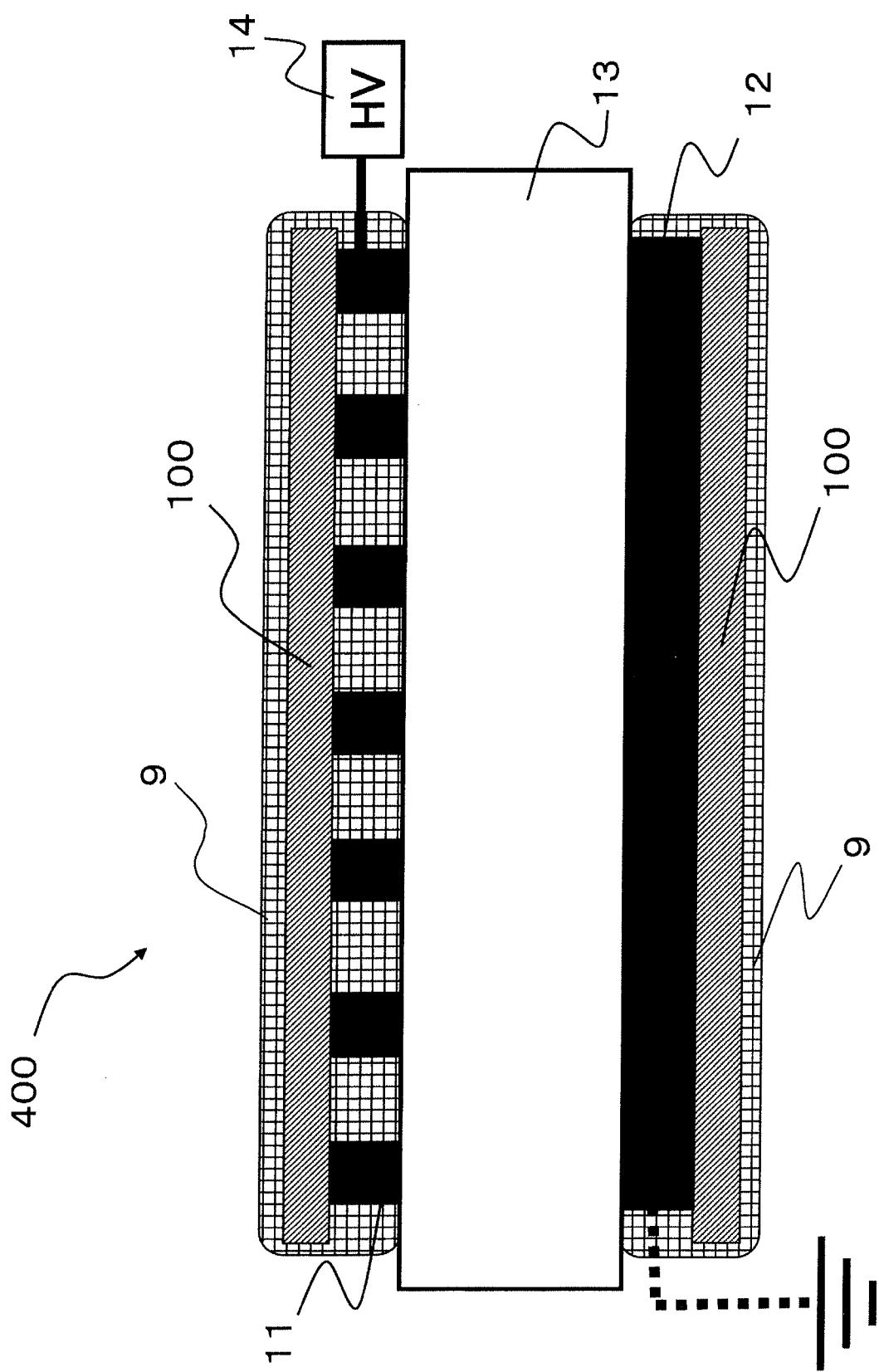
FIG. 8 is a schematic cross-sectional view of the gas treatment device according to the another embodiment of the present invention.

A sixth embodiment will next be described. FIG. 7 is a schematic view of a gas treatment device 400 of the present embodiment. FIG. 8 is a schematic view of the cross section of the gas treatment device 400 of the embodiment. FIG. 7 is an exploded perspective view illustrating a state of exploding the gas treatment device 400 having the structure shown in FIG. 8. In the gas treatment device 400, an application electrode 11 and a ground electrode 12 are provided on one face and the other face, respectively, of a plate-shaped or sheet-shaped dielectric material 13. In the structure, electrical discharging occurs to generate plasma on both the faces of the dielectric material 13. The gas treatment device 400 of the present embodiment is different from the gas treatment device 200 and the gas treatment device 300 in terms that a gas to be treated flows along the face of a catalyst medium 100, followed by treatment. Hereinafter, the configuration of the gas treatment device 400 of the present embodiment will be described, and the description of the same components as those in the above-described embodiments will be omitted by denoting the same symbols.

The application electrode 11 and the ground electrode 12 of the present embodiment are each a comb-teeth-shaped electrode that is formed of a large number of electrodes. The application electrode 11, the ground electrode 12, and the dielectric material 13 are arranged so that the dielectric material 13 comes into contact with at least one of the application electrode 11 and the ground electrode 12. Therefore, all the application electrode 11, the ground electrode 12, and the dielectric material 13 may be closely layered. It is preferable that the application electrode 11 and the ground electrode 12 be thin when the catalyst medium 100 corresponds to a plasma existence region 9.

When an AC high voltage is applied between the application electrode 11 and the ground electrode 12, creeping discharge occurs on the dielectric material 13 between the application electrode 11 and the dielectric material 13 to generate plasma. Similarly, creeping discharge occurs on the surface of the dielectric material 13 between the ground electrode 12 and the dielectric material 13 to generate plasma.

The catalyst medium 100 has the same configuration as the catalyst medium in the embodiments described above. As shown in FIG. 7, the catalyst medium 100 of the present embodiment is disposed outside the application electrode 11 and the ground electrode 12. As described above, in the gas treatment device 400, a gas to be treated does not flow through the catalyst medium 100, but flows along the catalyst medium 100 to accelerate an oxidation decomposition reaction into $CO_2$. Therefore, the catalyst medium 100 of the present embodiment may have a permeable structure used in the gas treatment devices 200 and 300, or a sheet-like structure or a plate-like structure without permeability.

When the catalyst medium 100 has an impermeable structure, irregularity may be formed on the surface by embossing. When irregularity is formed on the surface of the catalyst medium 100, an area in contact with a flowing gas is increased. Further, an oxidation decomposition reaction of a gas to be treated into $CO_2$ can be accelerated.

As shown in FIG. 7 (arrow c-d), a gas flows between the comb-teeth of the application electrode 11 along the comb-teeth during treatment of the gas in the gas treatment device 400 having the structure of the present embodiment. When a gas flows on the side of the ground electrode 12, a comb-teeth-shaped electrode may be permeable. A gas flows through the ground electrode 12 which is permeable along the direction of the comb-teeth of the application electrode 11 (as shown in an arrow c-d on the ground electrode 12 side). In this case, when the catalyst medium 100 is permeable, a gas can pass from the electrode sides through the adjacent catalyst medium 100, and a gas can pass from the catalyst medium 100 through the electrodes.

When the electrodes are thin, the plasma existence region 9 is also present outside the catalyst medium 100 as shown in FIG. 8. As shown in the arrow a-b of FIG. 7, a gas may flow outside the catalyst medium 100. Therefore, the gas flows while the gas comes into contact with the catalyst medium 100 disposed outside the application electrode 11 and the ground electrode 12. This accelerates an oxidation decomposition reaction of the gas to be treated into $CO_2$. Further, plasma generated by electrical discharging between the application electrode 11 and the dielectric material 13 and plasma generated by electrical discharging between the ground electrode 12 and the dielectric material 13 accelerate an oxidation decomposition reaction of CO into $CO_2$.

The present embodiment can provide the gas treatment device 400 that can accelerate the oxidation decomposition reaction of the gas to be treated into $CO_2$ to effectively oxidize and decompose a gas containing the gas to be treated into $CO_2$ and the like even when the gas flows along the surface of the catalyst medium 100 and is then treated. In particular, since the gas flows along the surface of the catalyst medium 100, the contact time of the gas with the catalyst medium 100 is increased, and the reaction accelerating effect due to the catalyst medium 100 can be obtained in the oxidation decomposition reaction of the gas to be treated into $CO_2$.

In the present embodiment, plasma can be generated by electrical discharging at both sides of the dielectric material 13, and the gas can be effectively treated by a set of the application electrode 11, the ground electrode 12, and the dielectric material 13.

The present embodiment has been described such that as the gas treatment device 400, the application electrode 11 is disposed on a side of one face of the dielectric material 13, the ground electrode 12 is disposed on a side of the other face of the dielectric material 13, and the catalyst medium 100 is disposed outside the electrodes. However, the present invention is not limited to the embodiment. The gas treatment device may have a structure in which the catalyst medium 100 comes into contact with the gas to be treated, and the gas flows through a space where plasma is generated by the application electrode 11, the ground electrode 12, and the dielectric material 13, so that plasma acts on the gas to be treated. Specifically, when catalyst fine particles 1-a are fixed to the surface of the dielectric material, and the dielectric material 13 has a function as the catalyst medium 100, the catalyst medium 100 can be omitted. Further, a method of disposing an electrode outside the catalyst medium 100, a method of fixing the catalyst medium 100 to the surface of an electrode, or a combination of two or more kinds thereof may be adopted. When the catalyst medium 100 and the dielectric material 13 are permeable, the gas to be treated may flow in a direction that is not along the comb-teeth and is perpendicular to the surface of the catalyst medium 100 or the dielectric material 13.

Seventh Embodiment

Figure 9:
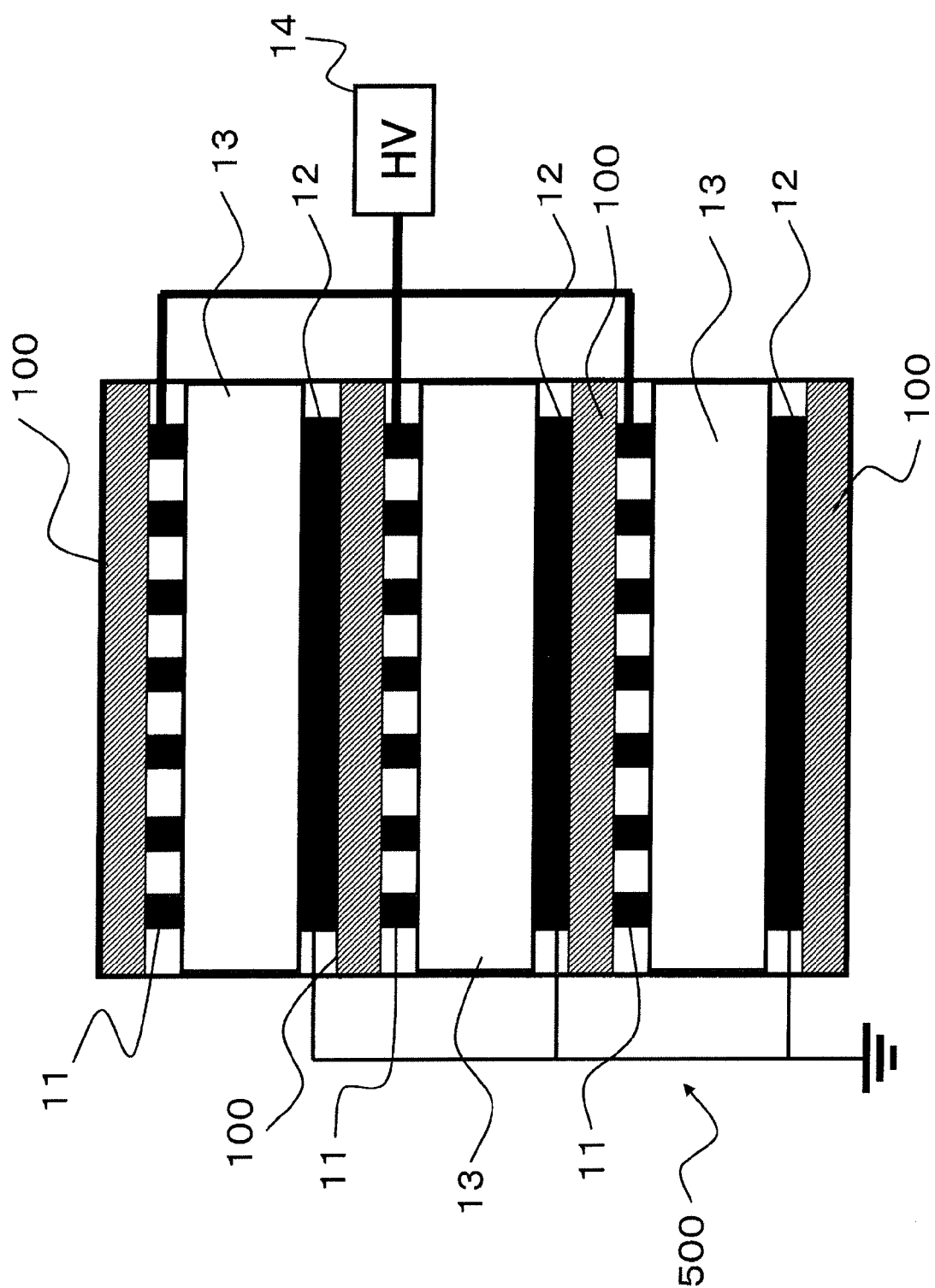
FIG. 9 is a schematic cross-sectional view of a gas treatment device according to another embodiment of the present invention.

A seventh embodiment will next be described. FIG. 9 is a view schematically illustrating a gas treatment device 500 of the embodiment. The gas treatment device 500 of the present embodiment is a modified example of the gas treatment device 400 of the sixth embodiment.

The gas treatment device 500 is configured by layering a plurality of gas treatment devices 400 of the sixth embodiment in a direction of layering electrodes (11 and 12) and a dielectric material 13. In the gas treatment device 500, a gas to be treated passes from a space between comb-teeth of the electrodes through a catalyst medium 100 similarly to the gas flow channel in the gas treatment device 400. Alternatively, when the gas treatment devices 400 are layered, a gap is provided between the devices so that a plasma existence region is not interrupted, and the gas flows through the gap. Use of the catalyst medium 100 and plasma accelerates an oxidation decomposition reaction of the gas to be treated into $CO_2$.

According to the present embodiment, the gas treatment device 500 is configured by layering a plurality of gas treatment devices 400. Therefore, an effect in which the gas to be treated in the gas to be treated can be effectively oxidized and decomposed can be obtained.

Eighth Embodiment

Figure 10:
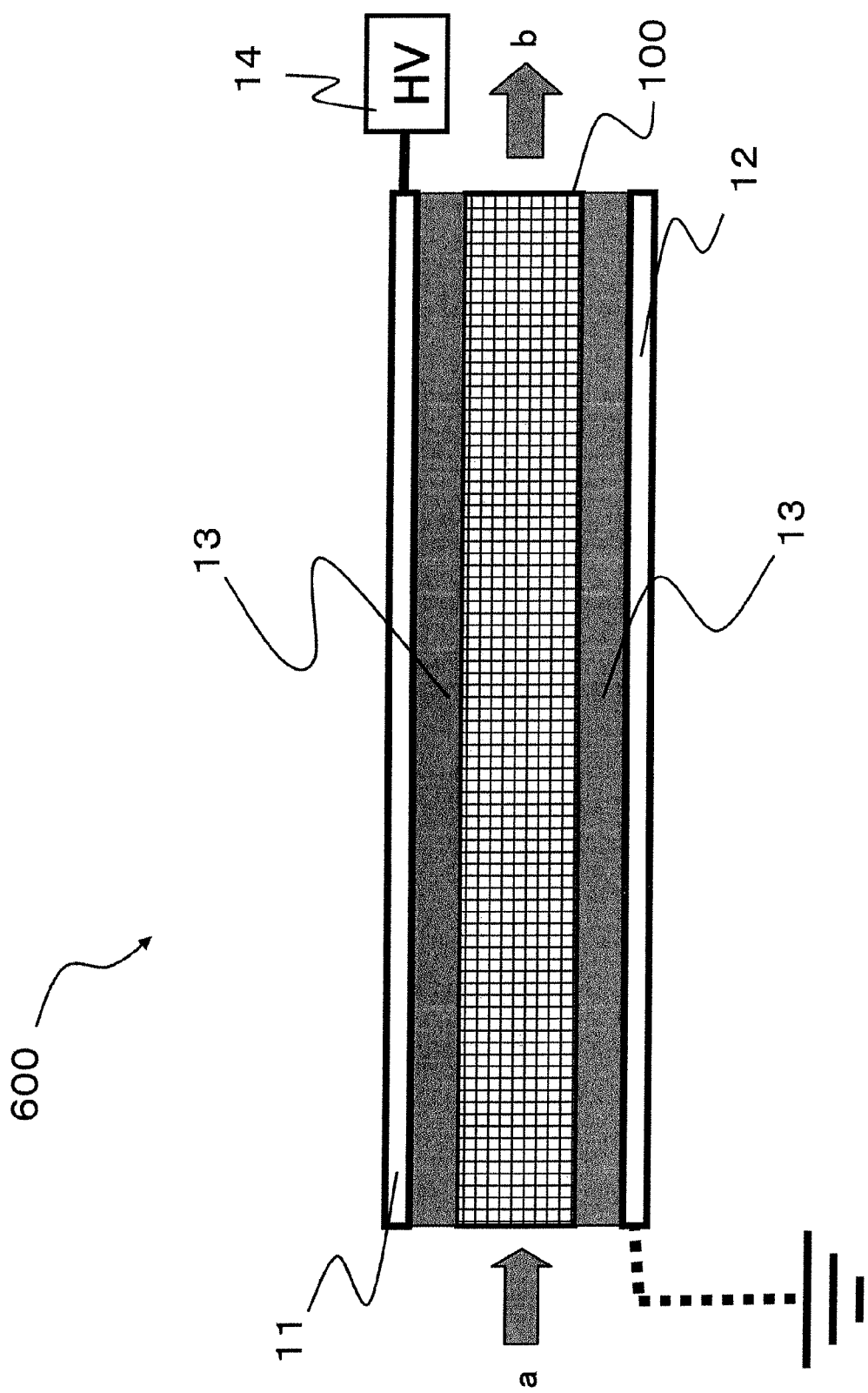
FIG. 10 is a schematic view of a gas treatment device according to another embodiment of the present invention.

An eighth embodiment will next be described. FIG. 10 is a view schematically illustrating a portion of the cross section of a gas treatment device 600 as one example of the embodiment. In the gas treatment device 600 of the present embodiment, plasma is generated by silent discharge.

In the gas treatment device 600, a non-thermal plasma reaction layer is provided with an application electrode 11, a ground electrode 12, and a dielectric material 13 by which plasma is generated with a voltage applied by a high voltage power supply 14, and a catalyst medium 100 is provided between both the electrodes. The electrodes, the dielectric material 13, and the catalyst medium 100 are closely layered. In FIG. 10, the ground electrode 11 and the ground electrode 12 are layered so as to each come into close contact with the dielectric material 13. However, the dielectric material 13 may be provided to only any one of them.

The catalyst medium 100 may or may not come into close contact with the dielectric material 13. When the catalyst medium comes into close contact with the dielectric material at both sides, the catalyst medium 100 needs to be permeable. When the catalyst medium 100 does not come into close contact with at least one dielectric material 13, the catalyst medium 100 may not be permeable. In the gas treatment device 600 of the present embodiment, a gas inflows in an arrow a direction of FIG. 10, and the gas is discharged from the other end side in an arrow b direction. Thus, the gas is decomposed. When the gas treatment device 600 has a multilayer structure, the gas treatment device 600 is provided so that a large amount of gas can be effectively decomposed and the gas to be treated can be effectively oxidized and decomposed according to use conditions such as an amount of gas to be treated and a flow rate. The catalyst medium 100 may be a single layer or a multiple layer, and can be optionally set.

Ninth Embodiment

Figure 11:
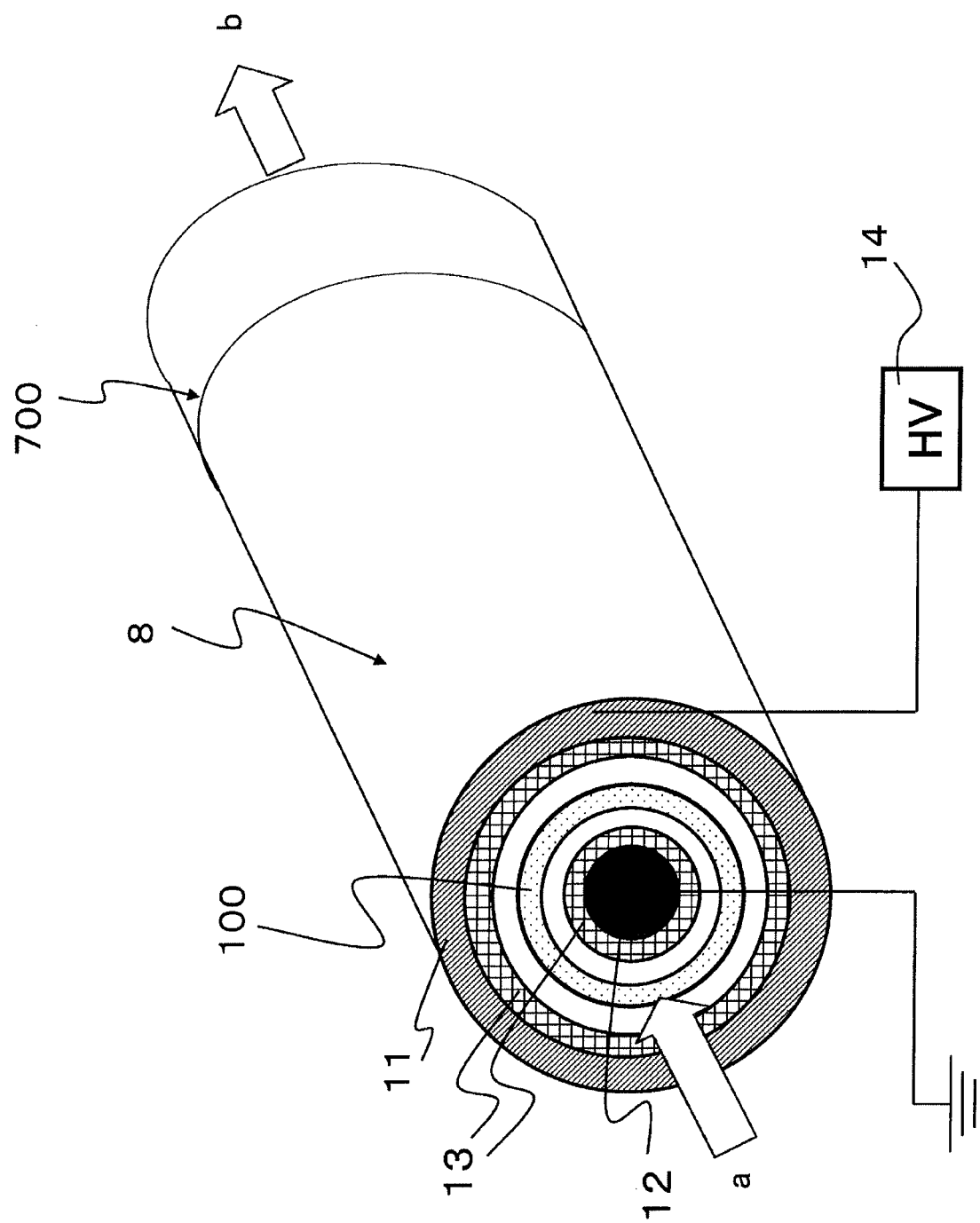
FIG. 11 is a schematic view of a gas treatment device according to another embodiment of the present invention.

A ninth embodiment will next be described. FIG. 11 is a view schematically illustrating a portion of the cross section of a gas treatment device 700 of the present embodiment. In the gas treatment device 700 of the present embodiment, plasma is generated by silent discharge to decompose a gas.

The gas treatment device 700 has a cylindrical structure in which a cylindrical application electrode 11, a cylindrical ground electrode 12, and a cylindrical catalyst medium 100 are layered outward in a radial direction in an annual ring shape. In a non-thermal plasma reaction layer 8 provided with an application electrode 11, a ground electrode 12, and a dielectric material 13 by which plasma is generated with a voltage applied by a high voltage power supply 14, a catalyst medium 100 is disposed between both the electrodes. In FIG. 11, the application electrode 11 and the ground electrode 12 are layered so as to each come into close contact with the dielectric material 13. However, the dielectric material 13 may be provided to only any one of them.

The catalyst medium 100 may or may not come into close contact with the dielectric material 13. In the gas treatment device 700, a gas inflows from one side of both circular ends, and the gas is discharged from the other side. Thus, the gas is decomposed. The plasma reaction layer 8 of the gas treatment device 700 may have an annual ring-shaped multilayer structure. In the multilayer structure, a large amount of gas can be effectively decomposed similarly to the multilayer structure of the gas treatment device 300 (FIG. 6) of the fifth embodiment or the gas treatment device 500 (FIG. 9) of the seventh embodiment. The plasma reaction layer 8 is provided so that the gas to be treated can be effectively oxidized and decomposed according to use conditions such as an amount of gas to be treated and a flow rate. In this case, one or more annual ring-shaped layers of the catalyst medium 100 may be optionally set.

Tenth Embodiment

Figure 12:
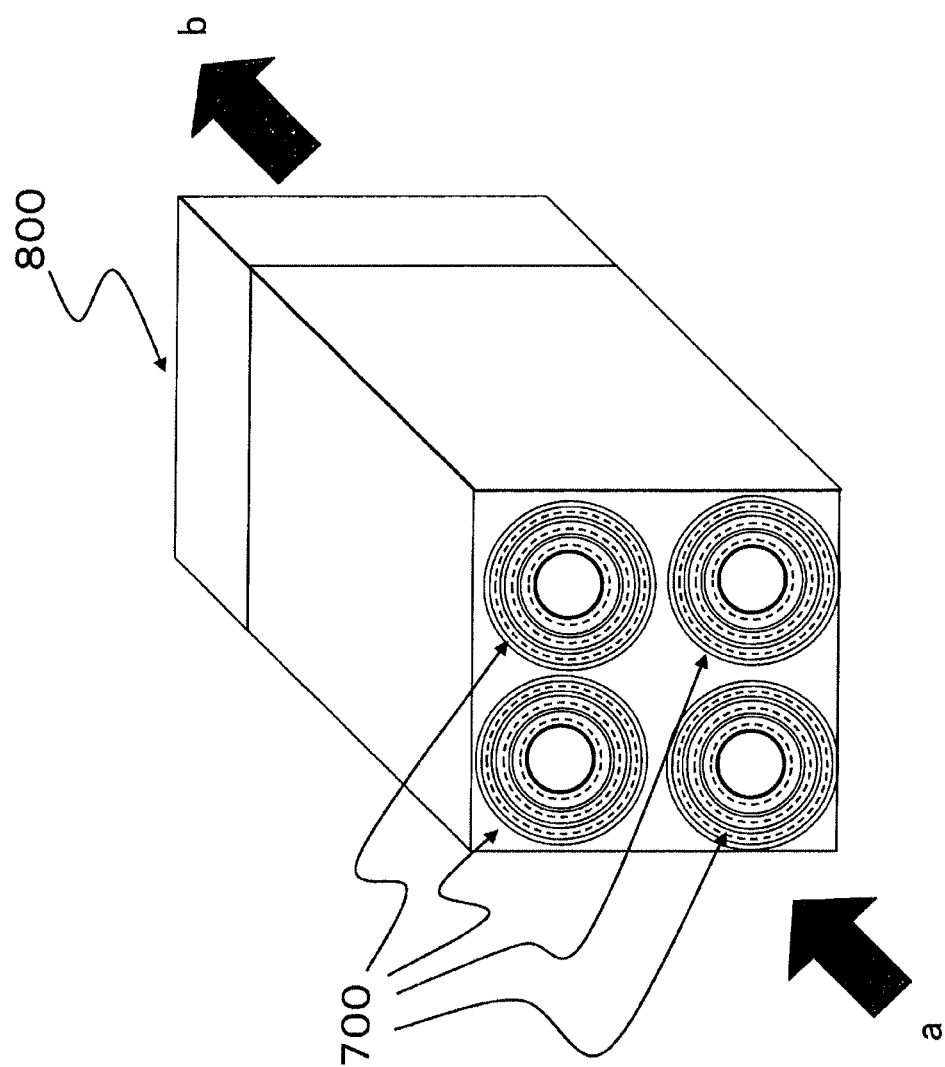
FIG. 12 is a schematic view of a gas treatment device according to another embodiment of the present invention.

A tenth embodiment will next be described. FIG. 12 is a schematic view illustrating a configuration of a gas treatment device 800 of the present embodiment. The gas treatment device 800 of the present embodiment is configured by combination of four cylindrical gas treatment devices 700 described in the ninth embodiment. Thus, a plurality of cylindrical gas treatment devices 700 are combined, so that a larger amount of gas can be treated.

In the gas treatment device 800 of FIG. 12, the gas treatment devices 700 are arranged in two rows and two columns. The present invention is not limited to this arrangement. The gas treatment devices 700 can be appropriately arranged according to a shape of a place where the gas treatment device 800 is disposed. For example, the plurality of gas treatment devices 700 may be arranged in one row or one column, or may be arranged so that the cross section of the gas treatment device 800 is a polygon such as a rectangle, a trapezoid, and a triangle, or a circle.

EXAMPLES

Hereinafter, the present invention will be described more specifically with reference to Examples. However, the present invention is not limited to these Examples.

(Production of Catalyst Medium 1)

The surface of alumina woven fabric (100 min×100 mm, available from NITIVY CO., LTD.) was washed with an alkaline detergent, and then washed with ion exchanged water. The alumina woven fabric was immersed in methanol, and then dried by a dryer. The alumina woven fabric was then immersed in an alumina sol (available from Nissan Chemical Industries, Ltd.), and excess alumina sol was removed by an air blower. The fabric was temporarily dried at 110° C. for 2 minutes, and then fired at 1,300° C. for 2 hours. A colloidal solution of platinum nanoparticles (available from TOKURIKI HONTEN CO., LTD., 5 nm) was applied to the treated alumina woven fabric by spraying. Next, the alumina woven fabric was dried at 600° C. for 4 hours to produce an alumina woven fabric (catalyst medium) having an α-alumina layer supporting platinum (corresponding to the catalyst medium of the second embodiment). At this time, the amount of platinum supported was measured by ICP, and found to be 1.5% by weight.

(Production of Catalyst Medium 2)

0.5% by weight of platinum bis(acetylacetonate) was mixed in α-alumina beads (available from TAIMEI CHEMICALS CO., LTD.) having a diameter of 500 μm and a purity of 99.99% by weight in a mortar to support platinum acetylacetonate on the surface of the alumina beads. Next, the alumina beads supporting platinum acetylacetonate was fired at 450° C. for 4 hours in an electric furnace to obtain a catalyst medium supporting 0.9% by weight of platinum (corresponding to the catalyst medium of the third embodiment). The catalyst was particles. Therefore, when the catalyst is actually used as the catalyst medium, a container is filled with the catalyst so that particles do not leak while the permeability is maintained in order to allow a gas to be treated to pass through the catalyst and to allow plasma to be present. In Examples, the device shown in FIG. 10 was used as the gas treatment device as described below. Therefore, the catalyst was wrapped in permeable mesh and then used as the catalyst medium.

(Production of Catalyst Medium 3)

99.7% by weight of aluminum plate (100 mm×100 mm) having a thickness of 0.2 mm was immersed in a molten salt produced by mixing $NaHSO_4$ and $NH_4HSO_4$ in a weight ratio of 1:1, and heating the mixture at 170° C. SUS304 was used as a counter electrode, the immersed aluminum was used as an anode, and an electrical potential of 170 V was applied to form an oxide film made from porous α-alumina. Next, the film was washed with water and dried. An aqueous solution of 2.0% by weight of $Pt(NO_2)_2(NH_3)_2$ was applied to the film by spraying, and fired at 450° C. for 4 hours in an electric furnace to obtain a plate-shaped catalyst medium supporting 1.2 $g/m^2$ platinum (corresponding to the catalyst medium of the fourth embodiment).

(Non-Thermal Plasma Reactor (Gas Treatment Device))

In Examples, as a device of generating non-thermal plasma, a gas treatment device 600 provided with a non-thermal plasma applying unit shown in FIG. 10 was used. A ground electrode 12 was formed of an alumina plate, an application electrode 11 was formed of a copper tape outside a dielectric material 13. The dielectric material 13 was α-alumina. A platinum-supporting catalyst medium 100 used in a reaction was disposed in a gap (1 mm) between the dielectric material 13 in contact with the application electrode 11 and another dielectric material 13 in contact with the ground electrode 12. The catalyst medium 100 is each of three kinds of catalyst media produced as described above.

In the gas treatment device 600, since the gas to be treated inflows in the arrow a direction of FIG. 10 and is discharged in the arrow b direction (so that the gas does not leak from a direction other than the arrow b direction), faces at both sides parallel to the gas flow direction (faces of the catalyst medium 100 at the front side and at the deeper side on the paper surface of FIG. 10) are coated with a housing made of vinyl chloride.

A voltage was applied between the application electrode 11 and the ground electrode 12 by the gas treatment device 600 to generate plasma in a plasma reaction layer formed by the application electrode 11 and the ground electrode 12. An ethylene ($C_2H_4$) gas was allowed to flow as the gas to be treated, and a test of removing (decomposing) $C_2H_4$ at room temperature was performed.

For the generation of plasma, an AC high voltage power supply provided with a function generator and a high-voltage amplifier was used. An applied voltage was set to a range of 0 to 20 kVpk-pk. A discharge output was determined by a V-Q Lissajous method.

In the $C_2H_4$ oxidation test, the initial concentration and the flow rate of $C_2H_4$ gas were adjusted to 50 ppm and 200 mL/min, respectively, so that the $C_2H_4$ gas was allowed to flow through the gas treatment device 600. The gas passing through the gas treatment device 600 was subjected to gas analysis using FTIR equipped with a gas cell with a light path length of 2.4 m, and the quantitative analysis of $C_2H_4$, CO, and $CO_2$ was performed.

The $C_2H_4$ gas was allowed to pass through the gas treatment device 600, and plasma was applied. The concentrations of $C_2H_4$, CO, and $CO_2$ 15 minutes after the application of plasma were used as gas concentrations after the reaction. A $C_2H_4$ removal ratio, a CO production ratio, and a $CO_2$ production ratio were determined as follows.

$C_2H_4$ removal ratio (%)={(initial concentration of $C_2H_4$−concentration of $C_2H_4$ after reaction)/ initial concentration of $C_2H_4$}×100

CO production ratio (%)=[(concentration of CO after reaction)/{(initial concentration of $C_2H_4$)×2}]× 100

$CO_2$ production ratio (%)=[(concentration of $CO_2$ after reaction)/{(initial concentration of $C_2H_4$)× 2}]×100

The ratio of a reaction intermediate other than CO or $CO_2$ produced from decomposed ethylene was determined as follows.

Reaction intermediate production ratio (%)=$C_2H_4$ removal ratio (%)−CO production ratio (%)− $CO_2$ production ratio (%)

Examples 1 to 21

As catalyst fine particles, $CeO_2$, PdO, and Au were used in addition to Pt. In Table 1, as the form of a catalyst medium, the form of alumina woven fabric formed by the α-alumina layer produced in Production of Catalyst Medium 1 (woven fabric form) is represented by a. The form of α-alumina particles having an average particle diameter of 500 μm produced in Production of Catalyst Medium 2 (beads form) is represented by b. The alumina plate (plate form) having an oxide film formed from a porous α-alumina similarly produced in Production of Catalyst Medium 3 is represented by c. The discharge outputs by a power supply 14 were 0.5, 1.0, and 3.0 W, and the output frequencies of the power supply were 0.05, 0.5, 0.75, 1.0, 1.5, 2.0, 3.0, 5.0, 7.0, and 9.0 kHz.

Comparative Examples 1 and 2

In Comparative Example 1, Pt was used as a catalyst, a (woven fabric form) was used as the form of the catalyst, and an ethylene gas was allowed to flow without application of plasma (using only the catalyst). In Comparative Example 2, a catalyst was not used, and plasma was applied at a discharge output of 1.0 W and an output frequency of the power supply of 1.0 kHz.

The details of conditions in Examples and Comparative Examples and the results of decomposition of ethylene are shown in Table 1.

$CO_2$ production ratio (%)={(concentration of $CO_2$ after reaction)/(initial concentration of CO)}×100

TABLE 1

| | CATALYST COMPONENT | CATALIST MEDIUM | DISCHARGE OUTPUT (W) | FREQUENCY (kHz) | ETHYLENE REMOVAL RATIO (%) | $CO_2$ PRODUCTION RATIO (%) | CO PRODUCTION RATIO (%) | INTERMEDIATE PRODUCTION RATIO (%) | GENERATED OZONE CONCENTRATION (ppm) |
|---|---|---|---|---|---|---|---|---|---|
| Example 1 | Pt/ | a | 0.5 | 0.5 | 90.4 | 90.4 | 0.0 | 0.0 | N.D[1] |
| Example 2 | $Al_2O_3$ | | | 0.75 | 88.2 | 88.2 | 0.0 | 0.0 | " |
| Example 3 | | | | 1.0 | 86.1 | 86.1 | 0.0 | 0.0 | " |
| Example 4 | | | | 1.5 | 84.3 | 84.3 | 0.0 | 0.0 | " |
| Example 5 | Pt/ | a | 1.0 | 0.75 | 93.3 | 93.3 | 0.0 | 0.0 | " |
| Example 6 | $Al_2O_3$ | | | 1.0 | 90.0 | 90.0 | 0.0 | 0.0 | " |
| Example 7 | | | | 1.5 | 87.2 | 87.2 | 0.0 | 0.0 | " |
| Example 8 | | | | 2.0 | 81.3 | 81.3 | 0.0 | 0.0 | " |
| Example 9 | | | | 3.0 | 72.1 | 72.1 | 0.0 | 0.0 | " |
| Example 10 | Pt/ | b | 1.0 | 1.0 | 87.5 | 87.5 | 0.0 | 0.0 | " |
| Example 11 | $Al_2O_3$ | c | | 1.0 | 86.8 | 86.8 | 0.0 | 0.0 | " |
| Example 12 | $CeO_2$ | a | 1.0 | 1.0 | 79.1 | 79.1 | 0.0 | 0.0 | " |
| Example 13 | PdO/$Al_2O_3$ | | | 1.0 | 67.2 | 67.2 | 0.0 | 0.0 | " |
| Example 14 | Au/$Al_2O_3$ | | | 1.0 | 58.5 | 58.5 | 0.0 | 0.0 | " |
| Example 15 | Pt/ | a | 3.0 | 1.0 | 85.3 | 85.3 | 0.0 | 0.0 | " |
| Example 16 | $Al_2O_3$ | | | 3.0 | 79.7 | 79.7 | 0.0 | 0.0 | " |
| Example 17 | | | | 5.0 | 51.9 | 51.9 | 0.0 | 0.0 | " |
| Example 18 | | | | 7.0 | 29.1 | 29.1 | 0.0 | 0.0 | " |
| Example 19 | Pt/ | a | 0.5 | 0.05 | 78.4 | 76.1 | 2.3 | 0.0 | 23.0 |
| Example 20 | $Al_2O_3$ | | 1.0 | 0.05 | 92.9 | 83.0 | 9.9 | 0.0 | 104.0 |
| Example 21 | | | 3.0 | 9 | 0.0 | 0.0 | 0.0 | 0.0 | N.D |
| Comparative Example 1 | Pt/$Al_2O_3$ | a | — | — | 0.0 | 0.0 | 0.0 | 0.0 | N.D |
| Comparative Example 2 | — | — | 1.0 | 1.0 | 97.3 | 17.3 | 24.8 | 55.2 | 206.0 |

[1]N.D (Not Detected): LOWER THAN DETECTION LIMIT

From the above results, it was confirmed that ethylene was not decomposed using only the catalyst (Comparative Example 1). Further, it was confirmed that ethylene was decomposed, but not completely oxidized and decomposed into $CO_2$ using only plasma (Comparative Example 2). Further confirmed was that a large amount of CO remained and a large amount of intermediate and ozone were produced. Moreover, it was confirmed that ethylene was not completely decomposed into $CO_2$ at a frequency lower than 0.5 kHz, CO remained, and ozone were produced. It was confirmed that at a frequency higher than 7 kHz, the removal ratio of ethylene was significantly decreased.

The CO gas as the gas to be treated was allowed to pass through the gas treatment device 600, and plasma was applied. The concentrations of CO and $CO_2$ 15 minutes after the application of plasma were used as gas concentrations after the reaction. A CO removal ratio and a $CO_2$ production ratio were determined as follows.

CO removal ratio (%)={(initial concentration of CO−concentration of CO after reaction)/(initial concentration of CO)}×100

Examples 22 to 33

As catalyst fine particles, Au was used. Supported zirconium was used. The discharge outputs by the power supply 14 were 0.5, 1.0, and 3.0 W, and the output frequencies of the power supply were 6, 7, 8, 9, 11, 12, 13, 14, and 15 kHz.

Comparative Examples 3 and 4

In Comparative Example 3, Au was used as a catalyst, a (woven fabric form) was used as the form of the catalyst, and a CO gas was allowed to flow without application of plasma (using only the catalyst). In Comparative Example 4, a catalyst was not used, and plasma was applied at a discharge output of 1.0 W and an output frequency of the power supply of 1.0 kHz.

The details of conditions in Examples and Comparative Examples and the results of CO gas treatment are shown in Table 2.

TABLE 2

| | CATALYST COMPONENT | CATALYST MEDIUM | DISCHARGE OUTPUT (W) | FREQUENCY (kHz) | CO REMOVAL RATIO (%) | $CO_2$ PRODUCTION RATIO (%) | INTERMEDIATE PRODUCTION RATIO (%) | GENERATED OZONE CONCENTRATION (ppm) |
|---|---|---|---|---|---|---|---|---|
| Example 22 | Au/ | a | 0.5 | 6.0 | 90.7 | 90.7 | 0.0 | N.D[1] |
| Example 23 | $ZrO_2$ | | | 7.0 | 90.6 | 90.6 | 0.0 | " |

TABLE 2-continued

| | CATALYST COMPONENT | CATALYST MEDIUM | DISCHARGE OUTPUT (W) | FREQUENCY (kHz) | CO REMOVAL RATIO (%) | $CO_2$ PRODUCTION RATIO (%) | INTERMEDIATE PRODUCTION RATIO (%) | GENERATED OZONE CONCENTRATION (ppm) |
|---|---|---|---|---|---|---|---|---|
| Example 24 | | | | 8.0 | 91.2 | 91.2 | 0.0 | " |
| Example 25 | | | 1.0 | 9.0 | 90.4 | 90.4 | 0.0 | " |
| Example 26 | | | | 11.0 | 89.8 | 89.8 | 0.0 | " |
| Example 27 | | | | 12.0 | 90.5 | 90.5 | 0.0 | " |
| Example 28 | | | 3.0 | 13.0 | 91.4 | 91.4 | 0.0 | " |
| Example 29 | | | | 14.0 | 90.7 | 90.7 | 0.0 | " |
| Example 30 | | | | 15.0 | 90.0 | 90.0 | 0.0 | " |
| Example 31 | Au/$ZrO_2$ | a | 0.5 | 0.05 | 90.2 | 90.2 | 0.0 | 321.0 |
| Example 32 | | | 1.0 | 0.1 | 91.6 | 91.6 | 0.0 | 524.0 |
| Example 33 | | | 3.0 | 0.05 | 91.8 | 91.8 | 0.0 | 1134.0 |
| Comparative Example 3 | Au/$ZrO_2$ | a | — | — | 85.8 | 85.8 | 0.0 | N.D |
| Comparative Example 4 | — | — | 1.0 | 1.0 | 0.0 | 0.0 | 0.0 | 352.0 |

[1])N.D (Not Detected): LOWER THAN DETECTION LIMIT

From the above results, production of an intermediate was not confirmed during oxidation of CO gas into $CO_2$. CO was oxidized without application of plasma using only the catalyst (Comparative Example 3). However, in a case of using plasma and a catalyst in combination, an increase in the CO removal ratio was confirmed. In a case of using only plasma (Comparative Example 4), oxidation of CO was not confirmed. Moreover, it was confirmed that CO was not completely decomposed into $CO_2$ at a frequency lower than 0.5 kHz (Examples 31 to 33), CO remained, and ozone was produced.

Subsequently, a CO gas was allowed to flow, and a CO oxidation test was performed at room temperature over time. In the CO oxidation test, the initial concentration and the flow rate of the CO gas were adjusted to 1,000 ppm and 500 mL/min, respectively, and the CO gas was allowed to flow through the gas treatment device 600. The gas passing through the gas treatment device 600 was subjected to gas analysis using FTIR equipped with a gas cell with a light path length of 2.4 m, and the quantitative analysis of CO and $CO_2$ was performed.

Example 34

Similarly to Example 22, Au/$ZrO_2$ was used as catalyst fine particles. The form of a catalyst medium was a (woven fabric form), the discharge output by the power supply 14 was 0.5 W, and the output frequency of the power supply was 6 kHz.

Comparative Example 5

Au was used as a catalyst, the form of the catalyst was a (woven fabric form), and plasma was not applied.

The details of conditions in Examples and Comparative Examples and the results of CO oxidation test over time are shown in Table 3.

TABLE 3

| | CATALYST COMPONENT | CATALYST MEDIUM | DISCHARGE OUTPUT (W) | FREQUENCY (kHz) | CO REMOVAL RATIO (%) GAS FLOW TIME (hr) | |
|---|---|---|---|---|---|---|
| | | | | | 0 | 20 |
| Example 34 | Au/$ZrO_2$ | a | 0.5 | 6.0 | 90.7 | 87.7 |
| Comparative Example 5 | Au/$ZrO_2$ | a | — | — | 85.8 | 60.3 |

In a case of using no plasma (Comparative Example 5), a decrease in CO removal ratio was confirmed.

An MEK ($CH_3COC_2H_5$) gas was allowed to flow through the gas treatment device 600, and plasma was applied. The concentrations of MEK, CO, and $CO_2$ 15 minutes after the application of plasma were used as gas concentrations after the reaction. A CO removal ratio and a $CO_2$ production ratio were determined as follows.

MEK removal ratio (%)={(initial concentration of MEK−Concentration of MEK after reaction)/(initial concentration of MEK)}×100 CO production ratio (%)=[(concentration of CO after reaction)/{(initial concentration of MEK)×4}]×100

$CO_2$ production ratio (%)=[(concentration of $CO_2$ after reaction)/{(initial concentration of MEK)×4}]×100

The ratio of a reaction intermediate other than CO or $CO_2$ produced from decomposed MEK was determined as follows.

Reaction intermediate production ratio (%)=MEK removal ratio (%)−CO production ratio (%)−$CO_2$ production ratio (%)

Examples 35 to 46

As catalyst fine particles, $CeO_2$ was used. The discharge outputs by the power supply 14 were 1.0, 2.0, 5.0, and 7.0 W, and the output frequencies of the power supply were 0.05, 1, 3, 5, 6, 8, 10, 15, and 20 kHz.

Comparative Examples 6 and 7

In Comparative Example 6, $CeO_2$ was used as a catalyst, the form of the catalyst was a (woven fabric form), and an MEK gas was allowed to flow without application of plasma (using only the catalyst). In Comparative Example 7, a catalyst was not used, and plasma was applied at a discharge output of 1.0 W and an output frequency of the power supply of 1.0 kHz.

The details of conditions in Examples and Comparative Examples and the results of decomposition of MEK are shown in Table 4.

CO production ratio (%)=[(Concentration of CO after reaction)/{(initial concentration of $C_7H_8$)×7}]×100

$CO_2$ production ratio (%)=[(concentration of $CO_2$ after reaction)/{(initial concentration of $C_7H_8$)×7}]×100

The ratio of a reaction intermediate other than CO or $CO_2$ produced from decomposed $C_7H_8$ gas was determined as follows.

Reaction intermediate production ratio (%)=$C_7H_8$ removal ratio (%)−CO production ratio (%)−$CO_2$ production ratio (%)

Examples 47 to 51

As catalyst fine particles, PdO was used. In Table 1, as the form of a catalyst medium, the form of alumina woven fabric formed by the α-alumina layer produced in Production of Catalyst Medium 1 (woven fabric form) is repre-

TABLE 4

| | CATALYST COMPONENT | CATALYST MEDIUM | DISCHARGE OUTPUT (W) | FREQUENCY (kHz) | MEK REMOVAL RATIO (%) | $CO_2$ PRODUCTION RATIO (%) | CO PRODUCTION RATIO (%) | INTERMEDIATE PRODUCTION RATIO (%) | GENERATED OZONE CONCENTRATION (ppm) |
|---|---|---|---|---|---|---|---|---|---|
| Example 35 | $CeO_2$ | a | 2.0 | 1.0 | 80.3 | 80.3 | 0.0 | 0.0 | N.D[1] |
| Example 36 | | | | 3.0 | 74.8 | 74.8 | 0.0 | 0.0 | " |
| Example 37 | | | | 5.0 | 54.2 | 54.2 | 0.0 | 0.0 | " |
| Example 38 | | | 5.0 | 3.0 | 91.3 | 91.3 | 0.0 | 0.0 | " |
| Example 39 | | | | 6.0 | 68.1 | 68.1 | 0.0 | 0.0 | " |
| Example 40 | | | | 8.0 | 55.5 | 55.5 | 0.0 | 0.0 | " |
| Example 41 | | | 7.0 | 8.0 | 91.5 | 91.5 | 0.0 | 0.0 | " |
| Example 42 | | | | 10.0 | 70.4 | 70.4 | 0.0 | 0.0 | " |
| Example 43 | | | | 15.0 | 51.1 | 51.1 | 0.0 | 0.0 | " |
| Example 44 | $CeO_2$ | a | 1.0 | 0.05 | 14.8 | 5.1 | 7.2 | 2.5 | 326.0 |
| Example 45 | | | 5.0 | 0.05 | 78.4 | 76.1 | 2.3 | 0.0 | 1432.0 |
| Example 46 | | | 1.0 | 20.0 | 0.0 | 0.0 | 0.0 | 0.0 | N.D |
| Comparative Example 6 | $CeO_2$ | a | — | — | 0.0 | 0.0 | 0.0 | 0.0 | " |
| Comparative Example 7 | — | | 1.0 | 1.0 | 33.2 | 3.5 | 13.3 | 16.4 | 296.0 |

[1]N.D (Not Detected): LOWER THAN DETECTION LIMIT

From the above results, it was confirmed that the MEK gas was not decomposed using only the catalyst (Comparative Example 6). Further, in a case of using only plasma (Comparative Example 7), it was confirmed that the MEK gas was decomposed, but not completely oxidized and decomposed into $CO_2$, a large amount of CO remained, and a large amount of intermediate and ozone were produced. Moreover, it was confirmed that the MEK gas was not completely decomposed at a frequency lower than 0.5 kHz, CO remained, and ozone were produced. It was confirmed that at a frequency higher than 15 kHz, the MEK gas was not decomposed at all.

Subsequently, toluene ($C_7H_8$) gas was allowed to flow through the gas treatment device 600, and plasma was applied. The concentrations of $C_7H_8$, CO, and $CO_2$ 15 minutes after the application of plasma was used as gas concentrations after the reaction. A $C_7H_8$ removal ratio, a CO production ratio, and a $CO_2$ production ratio were determined as follows.

$C_7H_8$ removal ratio (%)={(initial concentration of $C_7H_8$−concentration of $C_7H_8$ after reaction)/initial concentration of $C_7H_8$}×100 sented by a. The form of α-alumina particles having an average particle diameter of 500 μm produced in Production of Catalyst Medium 2 (beads form) is represented by b. The alumina plate (plate form) having an oxide film formed from a porous α-alumina similarly produced in Production of Catalyst Medium 3 is represented by c. The discharge outputs by the power supply 14 were 1.0, 5.0, and 7.0 W, and the output frequencies of the power supply were 0.5, 6.0, and 15.0 kHz.

Comparative Examples 8 and 9

PdO was used as a catalyst, the form of the catalyst was a (woven fabric form), and the output frequency of the power supply was 0.5 W.

The details of conditions in Examples and Comparative Examples and the results of decomposition of $C_7H_8$ are shown in Table 5.

TABLE 5

| | CATALYST COMPONENT | CATALYST MEDIUM | DISCHARGE OUTPUT (W) | FREQUENCY (kHz) | $C_7H_8$ REMOVAL RATIO (%) | $CO_2$ PRODUCTION RATIO (%) | CO PRODUCTION RATIO (%) | INTERMEDIATE PRODUCTION RATIO (%) | GENERATED OZONE CONCENTRATION (ppm) |
|---|---|---|---|---|---|---|---|---|---|
| Example 47 | PdO/ | a | 1.0 | 0.5 | 77.4 | 77.4 | 0.0 | 0.0 | N.D[1] |
| Example 48 | $ZrO_2$ | | 5.0 | 6.0 | 83.5 | 83.5 | 0.0 | 0.0 | " |
| Example 49 | | | 7.0 | 15.0 | 85.2 | 85.2 | 0.0 | 0.0 | " |
| Example 50 | PdO/ | a | 1.0 | 0.1 | 25.2 | 11.1 | 10.8 | 3.3 | 324.0 |
| Example 51 | $ZrO_2$ | | 7.0 | 20.0 | 0.0 | 0.0 | 0.0 | 0.0 | N.D |
| Comparative Example 8 | PdO/ $ZrO_2$ | a | — | — | 0.0 | 0.0 | 0.0 | 0.0 | " |
| Comparative Example 9 | — | — | 1.0 | 0.5 | 25.6 | 11.2 | 5.0 | 9.4 | 523.0 |

[1] N.D (Not Detected): LOWER THAN DETECTION LIMIT

From the above results, it was confirmed that the $C_7H_8$ gas was not decomposed using only the catalyst (Comparative Example 8). Further, it was confirmed that the $C_7H_8$ gas was decomposed, but not completely oxidized and decomposed into $CO_2$ using only plasma (Comparative Example 9), a large amount of CO remained, and a large amount of intermediate and ozone were produced. Moreover, it was confirmed that the $C_7H_8$ gas was not completely decomposed into $CO_2$ at a frequency lower than 0.5 kHz, CO remained, and ozone were produced. It was confirmed that at a frequency higher than 15 kHz, the $C_7H_8$ gas was not decomposed at all.

In Comparative Example 10, a PET nonwoven fabric was used instead of alumina woven fabric as the catalyst medium of Example 30. The catalyst media of Example 30 and Comparative Example 10 were used, a CO gas was allowed to flow, and plasma was applied for 4 hours. When a state of a substrate was observed, no change of the alumina woven fabric (Example 30) was found. However, the PET nonwoven fabric (Comparative Example 10) was deteriorated and low plasma resistance was confirmed.

REFERENCE SIGNS LIST

100 Catalyst medium
200 Gas treatment device
300 Gas treatment device according to another embodiment
400 Gas treatment device according to another embodiment
500 Gas treatment device according to another embodiment
600 Gas treatment device according to another embodiment
700 Gas treatment device according to another embodiment
800 Gas treatment device according to another embodiment
**1-*a*** Catalyst fine particle
**1-*b*** Inorganic fine particle
**1-*c*** Inorganic particle
2 Silane monomer
3 Chemical bond
4 Oxide film
5 Micropore
8 Discharge space
9 Plasma existence region
10 Substrate
11 Application electrode
12 Ground electrode
13 Dielectric material
14 Power supply

The invention claimed is:

1. A gas treatment method comprising:
generating plasma by discharging electricity at a discharge output of 3.0 W or less in a region where a catalyst medium for accelerating an oxidation decomposition reaction with a gas to be treated is disposed, said electrical discharging being performed by supplying AC power at an output frequency in a range of 6.0 kHz to 15 kHz, inclusive; and
passing the gas to be treated in the plasma to cause oxidation decomposition, the gas to be treated being an CO gas, and the catalyst medium being Au supported by $ZrO_2$.

2. The gas treatment method of claim 1, wherein said passing the gas to be treated in the plasma to cause oxidation decomposition is performed to remove at least 89.8% of CO.

3. The gas treatment method of claim 2, wherein said passing the gas to be treated in the plasma to cause oxidation decomposition is performed without producing any ozone.

* * * * *